"(12) United States Patent
Wallajapet et al.

US007012105B2

(10) Patent No.: US 7,012,105 B2
(45) Date of Patent: *Mar. 14, 2006

(54) STRUCTURE HAVING BALANCED PH PROFILE

(75) Inventors: Palani Raj Ramaswami Wallajapet, Wauwatosa, WI (US); Alice Y. Romans-Hess, Fremont, WI (US); Edwin T. Ta, Menasha, WI (US); Jian Qin, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/627,061

(22) Filed: Jul. 25, 2003

(65) Prior Publication Data

US 2004/0073181 A1 Apr. 15, 2004

Related U.S. Application Data

(63) Continuation of application No. 09/188,358, filed on Nov. 10, 1998, now Pat. No. 6,639,120, which is a continuation-in-part of application No. 08/989,555, filed on Dec. 12, 1997, now abandoned.

(51) Int. Cl.
*A61L 15/14* (2006.01)
*A61L 15/16* (2006.01)
*A61L 15/22* (2006.01)
*A61F 13/15* (2006.01)

(52) U.S. Cl. .................... 523/105; 523/111; 524/394; 524/424; 524/916; 525/418; 604/364; 604/372

(58) Field of Classification Search ................ 523/105, 523/111; 524/394, 424, 916; 525/418; 604/364, 604/372
See application file for complete search history.

(56) References Cited

U.S. PATENT DOCUMENTS

| | | |
|---|---|---|
| 2,586,883 A | 2/1952 | Stroh |
| 3,558,744 A | 1/1971 | Michaels et al. |
| 3,669,103 A | 6/1972 | Harper et al. |
| 3,794,034 A | 2/1974 | Jones, Sr. |
| 3,962,158 A | 6/1976 | Mima et al. |
| 4,104,214 A | 8/1978 | Meierhoefer |
| 4,200,557 A | 4/1980 | Chatterjee et al. |
| 4,440,541 A | 4/1984 | Berke |
| 4,454,268 A | 6/1984 | Otey et al. |
| 4,657,537 A | 4/1987 | Zimmerer |
| 4,685,909 A | 8/1987 | Berg et al. |
| 4,771,105 A | 9/1988 | Shirai et al. |
| 4,818,598 A | 4/1989 | Wong |
| 4,833,222 A * | 5/1989 | Siddall et al. .............. 526/200 |
| 4,842,593 A | 6/1989 | Jordan et al. |
| 5,011,864 A | 4/1991 | Nielsen et al. |
| 5,051,185 A | 9/1991 | Watanabe et al. |
| 5,126,382 A | 6/1992 | Hollenberg |
| 5,173,521 A | 12/1992 | Ishino |
| 5,258,421 A | 11/1993 | Lorenz et al. |
| 5,264,471 A | 11/1993 | Chmelir |
| 5,284,936 A | 2/1994 | Donachy et al. |
| 5,286,770 A | 2/1994 | Bastioli et al. |
| 5,340,853 A | 8/1994 | Chmelir et al. |
| 5,364,380 A | 11/1994 | Tanzer et al. |
| 5,420,197 A | 5/1995 | Lorenz et al. |
| 5,461,085 A | 10/1995 | Nagatomo et al. |
| 5,482,843 A | 1/1996 | Brzezinski |
| 5,487,895 A | 1/1996 | Dapper et al. |
| 5,496,933 A | 3/1996 | Kelkenberg |
| 5,550,189 A | 8/1996 | Qin et al. |
| 5,578,661 A | 11/1996 | Fox et al. |
| 5,610,208 A | 3/1997 | Dairoku et al. |
| 5,612,411 A | 3/1997 | Gross |
| 5,693,707 A | 12/1997 | Cheng et al. |
| 5,807,364 A | 9/1998 | Hansen |
| 5,856,410 A | 1/1999 | Carrico et al. |
| 6,639,120 B1 | 10/2003 | Wallajapet et al. |
| 2002/0058097 A1 * | 5/2002 | Beyer et al. ................ 426/590 |
| 2002/0147433 A1 * | 10/2002 | McOsker et al. ........... 604/364 |
| 2003/0125684 A1 | 7/2003 | Oin |

FOREIGN PATENT DOCUMENTS

| | | |
|---|---|---|
| EP | 0 763 364 A2 | 3/1997 |
| WO | WO 91/15250 A1 | 10/1991 |
| WO | WO 95/22358 A1 | 8/1995 |
| WO | WO 96/15163 A1 | 5/1996 |
| WO | WO 96/15180 A1 | 5/1996 |
| WO | WO 96/17681 A1 | 6/1996 |

OTHER PUBLICATIONS

Campbell, Neil A., *Biology*, The Benjamin/Cummings Publishing Company, Inc., 1987, pp. 45-48 and G-3.
Chang, Raymond, *Chemistry*, Second Edition, Random House. Inc., New York, 1984, pp. 141, 247 & 533.
Lide, David R., Ph. D., Editor, *CRC Handbook of Chemistry & Physics*, 74th Edition, CRC Press, Ann Arbor, Michigan, 1993-1994, pp. 7-1, 7-3, 7-30, 8-17, 8-18, 16-24, 16-25, and 16-26.

(Continued)

*Primary Examiner*—Tae H. Yoon
(74) *Attorney, Agent, or Firm*—Bryan R. Rosiejka

(57) ABSTRACT

Disclosed is an absorbent structure comprising an acidic or basic water-swellable, water-insoluble polymer, a basic or acidic second material, and, optionally, a buffering agent, wherein the absorbent structure exhibits desirable absorbent properties. Specifically, the present invention relates to an absorbent structure having the ability to absorb a large quantity of liquid while maintaining a substantially desired and balanced pH profile on or along the upper surface of the absorbent structure. The absorbent structure is useful in disposable absorbent products, such as those disposable absorbent products that are used to absorb body liquids.

12 Claims, 3 Drawing Sheets

OTHER PUBLICATIONS

Stoll, Vincent S. and John S. Blanchard, "Buffers: Principles and Practice," *Methods in Enzymology: vol. 182, Guide to Protein Purification*, edited by Murray P. Deutscher, Academic Press, Inc., 1990, pp. 24-26.

Chen, Chyi-Cheng, "Synthetic and Natural Polymers," Absorbency—Textile Science and Technology 7, edited by Pronoy K. Chatterjee, published by Elsevier, New York, 1985, p. 206.

* cited by examiner

STRUCTURE HAVING BALANCED PH PROFILE

This application is a continuation of U.S. patent application Ser. No. 09/188,358 entitled "Structure Having Balanced pH Profile" filed Nov. 10, 1998, now U.S. Pat. No. 6,639,120, which is a continuation-in-part of U.S. patent application Ser. No. 08/989,555 entitled "Structure Having Balanced pH Profile Comprising Acidic Polymer" filed Dec. 12, 1997, now abandoned. This application claims benefit to the filing date of both U.S. patent application Ser. No. 09/188,358 and U.S. patent application Ser. No. 08/989,555. The entirety of both U.S. patent application Ser. No. 09/188,358 and U.S. patent application Ser. No. 08/989,555 are hereby incorporated by reference.

BACKGROUND OF THE INVENTION

1. Field of the Invention

The present invention relates to an absorbent structure comprising an acidic or basic water-swellable, water-insoluble polymer, a basic or acidic material, and, optionally, a buffering agent, wherein the absorbent structure exhibits desirable absorbent properties. Specifically, the present invention relates to an absorbent structure having the ability to absorb a large quantity of liquid while maintaining a substantially desired and balanced pH profile on or along the upper surface of the absorbent structure. The absorbent structure is useful in disposable absorbent products, such as those disposable absorbent products that are used to absorb bodily liquids.

2. Description of the Related Art

The use of water-swellable, generally water-insoluble absorbent materials, commonly known as superabsorbents, in disposable absorbent products is known. Such absorbent materials are generally employed in disposable absorbent products such as diapers, training pants, adult incontinence products, and feminine care products in order to increase the absorbent capacity of such products while reducing their overall bulk. Such absorbent materials are generally present in disposable absorbent products in a fibrous matrix, such as a matrix of wood pulp fluff. A matrix of wood pulp fluff generally has an absorbent capacity of about 6 grams of liquid per gram of fluff. The superabsorbent materials generally have an absorbent capacity of at least about 10, preferably of about 20, and often of up to 100 times their weight in water. Clearly, incorporation of such absorbent materials in disposable absorbent products can reduce the overall bulk while increasing the absorbent capacity of such products.

The superabsorbent material commonly used in disposable absorbent products is the substantially neutralized form of a crosslinked polymer, such as the sodium salt of a crosslinked polyacrylic acid. The salt form of a crosslinked polymer is generally used since the capacity for the absorption of aqueous liquids of a crosslinked but substantially unneutralized polymer is typically very low as compared to the neutralized, or salt, form of the crosslinked polymer. However, one potential beneficial aspect of using the unneutralized form of a crosslinked polymer is that such a material has the capacity to exchange some of the cations present in urine and other body liquids that typically insult disposable absorbent products. In contrast, the substantially neutralized form of a crosslinked polymer generally does not allow for such ion-exchanging to occur.

It is, therefore, an object of the present invention to use the substantially unneutralized form of a crosslinked polymer in a disposable absorbent product in combination with another material which would neutralize the crosslinked polymer in situ when urine or other body liquids contact the disposable absorbent product. The use of the substantially unneutralized form of a crosslinked polymer would help reduce the ionic content of the body liquid through ion-exchange. The reduction in the ionic strength of a body liquid contacting a disposable absorbent product is generally beneficial in that the absorbent capacity of a crosslinked polymer is generally inversely related to the ionic strength of the liquid being absorbed. Furthermore, the synthesis of the substantially unneutralized form of a crosslinked polymer generally provides a better crosslinked polymeric network as compared to the synthesis of the substantially neutralized form of the crosslinked polymer, in that the formation of polymeric network defects is generally minimized which tends to increase the absorbent capacity of the crosslinked polymer. Therefore, another potential benefit of using the substantially unneutralized form of a crosslinked polymer, which is neutralized in situ, in a disposable absorbent product is the improvement in liquid absorption and distribution that occurs in the disposable absorbent product as problems caused by the rapid swelling of the substantially neutralized form of the crosslinked polymer can be avoided.

A complexity to the use of a substantially unneutralized form of a crosslinked polymer, with in situ neutralization of the crosslinked polymer, is the need to maintain a balanced pH profile on the surface of the disposable absorbent product. As the crosslinked polymer is being neutralized in situ after contact with a body liquid, temporary imbalances in pH can occur due to differences in the rate of dissolution or ionization of the material being used to neutralize the crosslinked polymer and the diffusion of the ionic species to the unneutralized sites in the crosslinked polymer which allows neutralization to occur. This temporary pH imbalance could result in an undesirable alkaline pH or an acidic pH in the disposable absorbent product next to a user's skin with the potential for skin irritation. As such, there is a need for controlling the pH in that portion of the disposable absorbent product that comes into contact with or is otherwise near or next to a wearer's or user's skin. By better controlling the pH in that portion of the disposable absorbent product that comes into contact with or is otherwise near or next to a user's skin, the incidence of skin irritation should be reduced.

It is, therefore, an object of the present invention to provide an absorbent structure that absorbs a large quantity of liquid, such as at about the same final capacity as compared to an absorbent structure comprising commercially available superabsorbent materials, wherein the absorbent structure maintains a substantially desired and balanced pH profile on or along the upper surface of the absorbent structure.

It is also an object of the present invention to provide an absorbent structure that comprises a substantially unneutralized form of a crosslinked polymer in combination with an inexpensive material that neutralizes the crosslinked polymer in situ since such an approach may reduce the overall cost of the absorbent structure.

It is also an object of the present invention to provide an absorbent structure that may be prepared simply and with a minimum of materials and additives so as to reduce the overall cost of preparing the absorbent structure as well as reduce the potential deleterious effect that such additives might have on the overall absorbent properties of the absorbent structure.

It is also an object of the present invention to provide an absorbent structure that exhibits unique properties so that such absorbent structure may be used in novel applications.

SUMMARY OF THE INVENTION

In one aspect, the present invention concerns an absorbent structure having the ability to absorb a large quantity of liquid while maintaining a substantially desired and balanced pH profile along the upper surface of the absorbent structure.

One embodiment of the present invention concerns an absorbent structure to be used in contact with human skin of a wearer, the absorbent structure comprising an upper surface oriented toward the skin of the wearer and a lower surface oriented away from the skin of the wearer, the absorbent structure further comprising:

a) a water-swellable, water-insoluble polymer having acidic functional groups, wherein the water-swellable, water-insoluble polymer has at least about 50 molar percent of the acidic functional groups in free acid form; and b) a basic material;

wherein the absorbent structure exhibits a Wicking Capacity value that is at least about 5 grams per gram of absorbent structure and exhibits a pH on the upper surface that remains within the range of about 3 to about 8.

Another embodiment of the present invention concerns an absorbent structure to be used in contact with human skin of a wearer, the absorbent structure comprising an upper surface oriented toward the skin of the wearer and a lower surface oriented away from the skin of the wearer, the absorbent structure further comprising:

a) a water-swellable, water-insoluble polymer having basic functional groups, wherein the water-swellable, water-insoluble polymer has at least about 50 molar percent of the basic functional groups in free acid form; and b) an acidic material;

wherein the absorbent structure exhibits a Wicking Capacity value that is at least about 5 grams per gram of absorbent structure and exhibits a pH on the upper surface that remains within the range of about 3 to about 8.

In another aspect, the present invention concerns a disposable absorbent product comprising an absorbent structure of the present invention that exhibits desired absorbent and pH properties.

In one embodiment of the present invention, a disposable absorbent product comprises a liquid-permeable topsheet, a backsheet attached to the topsheet, and an absorbent structure positioned between the liquid-permeable topsheet and the backsheet wherein the absorbent structure exhibits desired liquid absorbent and pH-control properties.

DETAILED DESCRIPTION OF THE PREFERRED EMBODIMENTS

Figure 1:
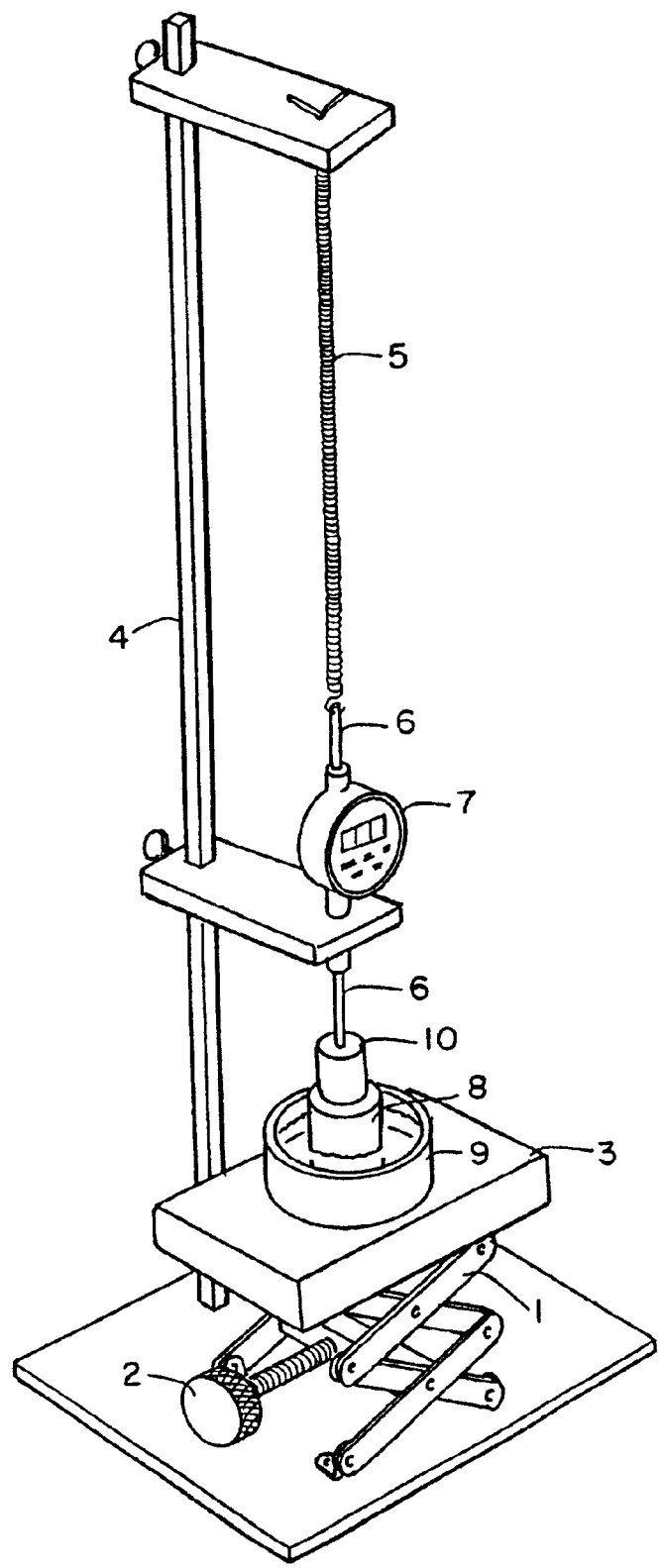
FIG. 1 is an illustration of the equipment employed in determining the Free Swell and Absorbency Under Load values of an absorbent composition.

It has now been discovered that an absorbent structure may be prepared that exhibits a relatively high total liquid absorption capacity as well as maintaining a substantially desired and balanced pH profile on or along the upper surface of the absorbent structure. In accordance with this invention, the absorbent structure comprises an upper surface oriented toward the skin of a wearer and a lower surface oriented away from the skin of the wearer. As used herein, "upper surface" means that surface of an absorbent structure which is intended to be worn toward or adjacent to the body of a wearer, while the "lower surface" is on the generally opposite side of the absorbent structure from the upper surface and is intended to be worn away from the wearer's body but towards, for example, any undergarments when the absorbent structure is worn.

The absorbent structure of the present invention generally comprises at least two different components. The first component is a water-swellable, water-insoluble polymer. As used in the absorbent structure of the present invention, the water-swellable, water-insoluble polymer to a large extent needs to provide the absorbent structure with its liquid-absorbing capacity. As such, the water-swellable, water-insoluble polymer needs to be effective to provide a desired amount of liquid-absorbing capacity to the absorbent structure.

As used herein, the terms "comprise", "comprises", "comprising", or similar terms, are intended to be synonymous with "including", "having", "containing", or "characterized by", and are intended to be inclusive or open-ended and are not intended-to exclude additional, unrecited components, elements, or method steps.

As used herein, the term "water-swellable, water-insoluble" is meant to refer to a material that, when exposed to an excess of water, swells to its equilibrium volume but does not dissolve into the solution. As such, a water-swellable, water-insoluble material generally retains its original identity or physical structure, but in a highly expanded state, during the absorption of the water and, thus, must have sufficient physical integrity to resist flow and fusion with neighboring particles.

As used herein, a material will be considered to be "water soluble" when it substantially dissolves in excess water to form a solution, thereby losing its initial, typically particulate, form and becoming essentially molecularly dispersed throughout the water solution. As a general rule, a water-soluble material will be free from a substantial degree of crosslinking, as crosslinking tends to render a material water insoluble.

One property of the water-swellable, water-insoluble polymer which is relevant to its effectiveness in providing a desired amount of liquid-absorbing capacity to the absorbent structure is its molecular weight. In general, a water-swellable, water-insoluble polymer with a higher molecular weight will exhibit a higher liquid-absorbing capacity as compared to a water-swellable, water-insoluble polymer with a lower molecular weight.

The water-swellable, water-insoluble polymer useful in the absorbent structure may generally have a wide range of molecular weights. A water-swellable, water-insoluble polymer having a relatively high molecular weight is often beneficial for use in the present invention. Nonetheless, a wide range of molecular weights is generally suitable for use in the present invention. Water-swellable, water-insoluble polymers suitable for use in the present invention will beneficially have a weight average molecular weight greater than about 100,000, more beneficially greater than about 200,000, suitably greater than about 500,000, more suitably greater than about 1,000,000, and up to about 10,000,000. Methods for determining the molecular weight of a polymer are known to those skilled in the art.

It is sometimes more convenient to express the molecular weight of a polymer in terms of its viscosity in a 1.0 weight percent aqueous solution at 25° C. Polymers suitable for use in the present invention will suitably have a viscosity in a 1.0 weight percent aqueous solution at 25° C. of from about 100 centipoise (100 mPa.s) to about 80,000 centipoise (80,000 mPa.s), more suitably from about 500 centipoise (500 mPa.s) to about 80,000 centipoise (80,000 mPa.s), and most suitably from about 1,000 centipoise (1,000 mPa.s) to about 80,000 centipoise (80,000 mPa.s).

The water-swellable, water-insoluble polymer useful in the absorbent composition will generally be crosslinked. The amount of crosslinking should generally be above a minimum amount sufficient to make the polymer water-insoluble but also below some maximum amount so as to allow the polymer to be sufficiently water swellable so that the water-swellable, water-insoluble polymer absorbs a desired amount of liquid.

Crosslinking of the polymer may generally be achieved by either of two different types of crosslinking agents. The first type of crosslinking agent is a polymerizable crosslinking agent. Suitable polymerizable crosslinking agents are generally reactive to the monomer or monomers used to prepare the polymer and, thus, generally comprise at least two functional groups that are capable of reacting with the monomers. Examples of suitable polymerizable crosslinking agents include ethylenically unsaturated monomers, such as N,N'-methylene bis-acrylamide, for free radical polymerization and polyamines or polyols for condensation polymerization.

The second type of crosslinking agent is a latent crosslinking agent. Latent crosslinking agents generally can be either polymerizable or non-polymerizable. The non-polymerizable crosslinking agents generally do not take part in the overall polymerization process but, instead, are reactive to the polymer at a later point in time when a proper crosslinking condition is provided. The polymerizable crosslinking agents do take part in the overall polymerization process but generally do not cause intermolecular crosslinking. The intermolecular crosslinking generally only occurs at a later point in time when a proper crosslinking condition is provided. Suitable post treatment conditions include using heat treatment, such as a temperature above about 60° C., exposure to ultraviolet light, exposure to microwaves, steam or high humidity treatment, high pressure treatment, or treatment with an organic solvent.

Latent non-polymerizable crosslinking agents suitable for use in the present invention are generally water soluble. A suitable latent non-polymerizable crosslinking agent is an organic compound having at least two functional groups or functionalities capable of reacting with any carboxyl, carboxylic, amino, or hydroxyl groups on the polymer. Examples of suitable latent non-polymerizable crosslinking agents include, but are not limited to, diamines, polyamines, diols, polyols, polycarboxylic acids, and polyoxides. Another suitable latent non-polymerizable crosslinking agent comprises a metal ion with more than two positive charges, such as $Al^{3+}$, $Fe^{3+}$, $Ce^{3+}$, $Ce^{4+}$, $Ti^{4+}$, $Zr^{4+}$, and $Cr^{3+}$.

When the polymer is a cationic polymer, a suitable latent non-polymerizable crosslinking agent is a polyanionic material such as sodium polyacrylate, carboxymethyl cellulose, or polyphosphate.

Latent polymerizable crosslinking agents suitable for use in the present invention are generally water soluble and reactive to the monomer or monomers used to prepare the water-swellable, water-insoluble polymer. The latent polymerizable crosslinking agents generally contain at least one functional group or functionality capable of reacting with the monomer or monomers and at least one functional group or functionality capable of reacting with any carboxyl, carboxylic, amino, or hydroxyl groups on the polymer. Examples of suitable latent polymerizable crosslinking agents include, but are not limited to, ethylene glycol vinyl ether, amino propanol vinyl ether, diethylamino ethyl methacrylate, allylamine, methylallylamine, ethylallylamine.

In one embodiment of the present invention, the water-swellable, water-insoluble polymer useful in the absorbent structure will be acidic in nature. As used herein, an "acidic" material is intended to refer to a material that may act as an electron acceptor and which, in an aqueous solution, exhibits a pH between about 0 to 7. Suitably, the pH is measured at about 25° C. Methods of measuring the pH of an aqueous solution are well known in the art.

In general, acidic, water-swellable, water-insoluble polymers useful in the absorbent structure may be either strongly or weakly acidic in nature. In general, an acidic, water-swellable, water-insoluble polymer that is strongly acidic will exhibit a pKa less than about 2. In general, an acidic, water-swellable, water-insoluble polymer that is weakly acidic will exhibit a pKa that is greater than about 2. As such, acidic, water-swellable, water-insoluble polymers useful in the absorbent structure may exhibit a broad range of pKa values, but will beneficially have a pKa between about 0 to about 12, more beneficially between about 2 to about 10, and suitably between about 3 to about 7. As will be appreciated by one skilled in the art, a monobasic acid will generally have a single pKa value whereas multibasic acids will generally have multiple pKa values. Unless indicated otherwise herein, a reference to the pKa value of a multibasic acid is intended to refer to the $pKa_1$ value of the multibasic acid.

It may sometimes be more convenient to measure the pKa of the monomer or monomers used to prepare a polymer. Although the pKa of the monomer or monomers and the polymer prepared from such monomers may not be identical, such pKa values should be substantially similar. As such, acidic, water-swellable, water-insoluble polymers useful in the absorbent structure may be prepared from a single monomer or a combination of monomers that exhibit a broad range of pKa values, but such monomers will beneficially have a pKa between about 0 to about 12, more beneficially between about 2 to about 10, and suitably between about 3 to about 7.

The pKa of an acid represents the extent of dissociation of or, in other words, the strength of the acid and is intended herein to be measured at the conditions, such as at a specific temperature, under which the water-swellable, water-insoluble polymer is being used. Suitably, the pKa is measured at about 25° C. In general, the weaker the acid, the higher the pKa value will be. The pKa values for many acids at various temperatures are well known and may be found in any of many available references, such as in the CRC Handbook of Chemistry & Physics, 75th Edition, edited by David R. Lide, CRC Press (1994).

Suitable acidic, water-swellable, water-insoluble polymers will include functional groups that are capable of acting as acids. Such functional groups include, but are not limited to, carboxyl groups, sulfonic groups, sulphate groups, sulfite groups, and phosphate groups. Suitably, the functional groups are carboxyl groups. Generally, the functional groups are attached to a crosslinked base polymer. Suitable base polymers include polyacrylamides, polyvinyl alcohols, ethylene maleic anhydride copolymer, polyvinylethers, polyacrylamido methylpropane sulfonic acid, polyacrylic acids, polyvinylpyrrolidones, polyvinylmorpholines, and copolymers of the preceding polymers. Natural based polysaccharide polymers may also be used and include carboxymethyl celluloses, carboxymethyl starches, hydroxypropyl celluloses, algins, alginates, carrageenans, acrylic grafted starches, acrylic grafted celluloses, and copolymers of the preceding polymers. Synthetic polypeptides can also be used such as polyaspartic acid and polyglutamic acid.

The acidic, water-swellable, water-insoluble polymer generally needs to be in its free acid form. In general, it is desired that the acidic, water-swellable, water-insoluble polymer beneficially have at least about 50 molar percent, more beneficially at least about 70 molar percent, suitably at least about 80 molar percent, more suitably at least about 90 molar percent, and most suitably substantially about 100 molar percent of its acidic functional groups in free acid form. Alternatively, then, the acidic, water-swellable, water-insoluble polymer should not be substantially neutralized when used in the absorbent structure of the present invention. In general, it is desired that the acidic, water-swellable, water-insoluble polymer have a degree of neutralization of its acidic functional groups that is beneficially less than about 50 molar percent, more beneficially less than about 30 molar percent, suitably less than about 20 molar percent, more suitably less than about 10 molar percent, and most suitably substantially about 0 molar percent.

Commercially available superabsorbents are generally in a substantially neutralized or salt form. This is because, in general, in order to have a relatively high capacity for liquid absorption, a water-swellable, water-insoluble polymer must be a polyelectrolyte. However, as discussed herein, the acidic water-swellable, water-insoluble polymers useful in the present invention are substantially in their free acid form. Therefore, such acidic water-swellable, water-insoluble polymers in their free acid form generally do not have, on their own, a relatively high capacity for liquid absorption.

It has been discovered in the present invention, however, that when such an acidic water-swellable, water-insoluble polymer, substantially in its free acid form, is combined or mixed with a basic second material, the resulting combination or mixture will exhibit a relatively high capacity for liquid absorption. This is believed to be because as the mixture is placed in an aqueous solution, the acidic water-swellable, water-insoluble polymer, substantially in its free acid form, reacts with the basic second material, and the chemical equilibrium is in favor of converting the acidic water-swellable, water-insoluble polymer from its free acid form to its respective salt form. As such, the mixture comprising the substantially neutralized water-swellable, water-insoluble polymer will now exhibit a relatively high capacity for liquid absorption. In addition, the conversion of the water-swellable, water-insoluble polymer, from its free acid form to its respective salt form in an electrolyte-containing solution, such as an aqueous sodium chloride solution or urine, can have a substantial desalting effect on the electrolyte-containing solution, thereby improving the liquid-absorbing performance of the mixture comprising the water-swellable, water-insoluble polymer by alleviating any salt-poisoning effect.

In another embodiment of the present invention, the water-swellable, water-insoluble polymer useful in the absorbent structure will be basic in nature. As used herein, a "basic" material is intended to refer to a material that may act as an electron donor and which, in an aqueous solution, exhibits a pH between 7 to about 14. Suitably, the pH is measured at about 25° C. Methods of measuring the pH of an aqueous solution are well known in the art.

In general, basic, water-swellable, water-insoluble polymers useful in the absorbent structure may be either strongly or weakly basic in nature. In general, a basic, water-swellable, water-insoluble polymer that is strongly basic will exhibit a pKa greater than about 12. In general, a basic, water-swellable, water-insoluble polymer that is weakly basic will exhibit a pKa that is less than about 12. As such, basic, water-swellable, water-insoluble polymers useful in the absorbent structure may exhibit a broad range of pKa values, but will beneficially have a pKa between about 2 to about 14, more beneficially between about 4 to about 12, and suitably between about 7 to about 11. As will be appreciated by one skilled in the art, a monobasic base will generally have a single pKa value whereas multibasic bases will generally have multiple pKa values. Unless indicated otherwise herein, a reference to the pKa value of a multibasic base is intended to refer to the $pka_1$ value of the multibasic base.

It may sometimes be more convenient to measure the pKa of the monomer or monomers used to prepare a polymer. Although the pKa of the monomer or monomers and the polymer prepared from such monomers may not be identical, such pKa values should be substantially similar. As such, basic, water-swellable, water-insoluble polymers useful in the absorbent structure may be prepared from a single monomer or a combination of monomers that exhibit a broad range of pKa values, but such monomers will beneficially have a pKa between about 2 to about 14, more beneficially between about 4 to about 12, and suitably between about 7 to about 11.

The pKa of an base represents the extent of dissociation of or, in other words, the strength of the base and is intended herein to be measured at the conditions, such as at a specific temperature, under which the water-swellable, water-insoluble polymer is being used. Suitably, the pKa is measured at about 25° C. In general, the weaker the base, the lower the pKa value will be. The pKa values for many bases at various temperatures are well known and may be found in any of many available references, such as in the CRC Handbook of Chemistry & Physics, $75^{th}$ Edition, edited by David R. Lide, CRC Press (1994).

Suitable basic water-swellable, water-insoluble polymers will include functional groups that are capable of acting as bases. Such functional groups include, but are not limited to, primary, secondary, or tertiary amino groups, imino groups, imido groups, amido groups, and quaternary ammonium groups. Suitably the functional groups are primary amino groups or quaternary ammonium groups. Generally, the functional groups are attached to a crosslinked base polymer. Suitable base polymers include polyamines, polyethyleneimines, polyacrylamides, polydiallyl dimethyl ammonium hydroxide, and polyquaternary ammoniums, and copolymers thereof. Natural based polysacchande polymers may also be used and include chitin and chitosan. Synthetic polypeptides can also be used such as polyasparagines, polyglutamines, polylysines, and polyarginines.

The basic, water-swellable, water-insoluble polymer generally needs to be in its free base form. In general, it is desired that the basic, water-swellable, water-insoluble polymer beneficially have at least about 50 molar percent, more beneficially at least about 70 molar percent, suitably at least about 80 molar percent, more suitably at least about 90 molar percent, and most suitably substantially about 100 molar percent of its basic functional groups in free base form. Alternatively, then, the basic, water-swellable, water-insoluble polymer should not be substantially neutralized when used in the absorbent structure of the present invention. In general, it is desired that the basic, water-swellable, water-insoluble polymer have a degree of neutralization of its basic functional groups that is beneficially less than about 50 molar percent, more beneficially less than about 30 molar percent, suitably less than about 20 molar percent, more suitably less than about 10 molar percent, and most suitably substantially about 0 molar percent.

Commercially available superabsorbents are generally in a substantially neutralized or salt form. This is because, in general, in order to have a relatively high capacity for liquid absorption, a water-swellable, water-insoluble polymer must be a polyelectrolyte. However, as discussed herein, the basic water-swellable, water-insoluble polymers useful in the present invention are substantially in their free base form. Therefore, such basic water-swellable, water-insoluble polymers in their free base form generally do not have, on their own, a relatively high capacity for liquid absorption.

It has been discovered in the present invention, however, that when such a basic water-swellable, water-insoluble polymer, substantially in its free base form, is combined or mixed with an acidic second material, the resulting combination or mixture will exhibit a relatively high capacity for liquid absorption. This is believed to be because as the mixture is placed in an aqueous solution, the basic water-swellable, water-insoluble polymer, substantially in its free base form, reacts with the acidic second material, and the chemical equilibrium is in favor of converting the basic water-swellable, water-insoluble polymer from its free base form to its respective salt form. As such, the mixture comprising the substantially neutralized water-swellable, water-insoluble polymer will now exhibit a relatively high capacity for liquid absorption. In addition, the conversion of the water-swellable, water-insoluble polymer, from its free base form to its respective salt form in an electrolyte-containing solution, such as an aqueous sodium chloride solution or urine, can have a substantial desalting effect on the electrolyte-containing solution, thereby improving the liquid-absorbing performance of the mixture comprising the water-swellable, water-insoluble polymer by alleviating any salt-poisoning effect.

In contrast to the above, it has been found that a single material or polymer, comprising both acidic and basic functional groups within its molecular structure, will not exhibit the desired absorbent properties described herein. This is believed to be because such acidic and basic functional groups within a single molecular structure will typically react with each other and might result in an over-crosslinked polymer structure. As such, it generally is not possible to prepare the absorbent structure of the present invention by preparing a copolymer from acidic and basic monomers or by preparing a molecular level dispersion, such as in an aqueous solution, of water-soluble acidic and basic materials since during such copolymerization or molecular level dispersion the acidic and basic materials will typically react with each other and crosslink.

The acidic or basic water-swellable, water-insoluble polymer may generally be used in the absorbent structure in a variety of forms. Examples of forms that the acidic or basic water-swellable, water-insoluble polymer may take include particles, flakes, fibers, films, and nonwoven structures. When the absorbent structure is used in disposable absorbent products, it is generally desired that the acidic or basic water-swellable, water-insoluble polymer be in the form of discrete particles, fibers, or flakes in a fibrous matrix. When in the form of a particle, it is generally desired that the particle have a maximum cross-sectional dimension beneficially within the range from about 50 micrometers to about 2,000 micrometers, suitably within the range from about 100 micrometers to about 1,000 micrometers, and more suitably within the range from about 300 micrometers to about 600 micrometers.

When the first component to be used in the absorbent structure of the present invention is an acidic water-swellable, water-insoluble polymer, the second component to be used in the absorbent structure of the present invention is a basic material. As used herein, a "basic" material is intended to refer to a material that may act as an electron donor and which, in an aqueous solution, exhibits a pH between 7 to about 14. Suitably, the pH is measured at about 25° C. Examples of suitable basic second materials include, but are not limited to, polymeric basic materials such as polyamines, polyimines, polyamides, polyquaternary ammoniums, chitins, chitosans, polyasparagines, polyglutamines, polylysines, and polyarginines; organic basic materials such as organic salts such as sodium citrate and aliphatic and aromatic amines, imines, and amides; and inorganic bases such as metallic oxides, such as calcium oxide and aluminum oxide; hydroxides, such as barium hydroxide; salts such as sodium carbonate, sodium bicarbonate, and calcium carbonate; and mixtures thereof. The basic second material can generally be either a strong or a weak base. However, the strength of the basicity of the basic second material has been found to potentially affect the liquid absorption rate of the absorbent structure. Generally, an absorbent structure comprising a relatively stronger basic second material will exhibit a relatively faster liquid absorption rate as compared to an absorbent structure comprising a relatively weaker basic second material.

In general, basic second materials useful in the absorbent structure may be either strongly or weakly basic in nature. In general, a basic second material that is strongly basic will exhibit a pKa value greater than about 12. In general, a basic second material that is weakly basic will exhibit a pKa that is less than about 12. As such, basic second materials useful in the absorbent structure may exhibit a broad range of pKa values, but will beneficially have a pKa between about 4 to about 14, more beneficially between about 5 to about 14, and suitably between about 8 to about 14.

In one beneficial embodiment of the present invention, the basic second material can also suitably be a water-swellable, water-insoluble polymer. In such an embodiment, both the acidic water-swellable, water-insoluble polymer and the basic, water-swellable, water-insoluble polymeric second material can be used to contribute to the total liquid absorptive capacity of the absorbent structure, thereby potentially achieving an overall higher liquid absorptive capacity of the absorbent structure as compared to the use of a basic second material that is not a water-swellable, water-insoluble polymer.

It may sometimes be more convenient to measure the pKa of the monomer or monomers used to prepare a polymer. Although the pKa of the monomer or monomers and the polymer prepared from such monomers may not be identical, such pKa values should be substantially similar. As such, basic, water-swellable, water-insoluble polymers useful in the absorbent structure may be prepared from a single monomer or a combination of monomers that exhibit a broad range of pKa values, but such monomers will beneficially have a pKa between about 4 to about 14, more beneficially between about 5 to about 14, and suitably between about 8 to about 14.

The pKa of a base represents the extent of dissociation of or, in other words, the strength of the base and is intended herein to be measured at the conditions, such as at a specific temperature, under which the base is being used. Suitably, the pKa is measured at about 25° C. In general, the weaker the base, the lower the pKa value will be. The pKa values for many bases at various temperatures are well known and may be found in any of many available references, such as in the CRC Handbook of Chemistry & Physics, 75$^{th}$ Edition, edited by David R. Lide, CRC Press (1994).

Suitable basic second materials will include functional groups that are capable of acting as bases. Such functional groups include, but are not limited to, primary, secondary, or tertiary amino groups, imino groups, imido groups, and amido groups. Suitably the functional groups are amino groups. When the basic second material is a water-swellable, water-insoluble polymer, the functional groups are generally attached to a crosslinked base polymer. Suitable base polymers include polyamines, polyimines, polyamides, and polyquaternary ammoniums, and copolymers thereof. Natural based polysaccharide polymers may also be used and include chitin and chitosan. Synthetic polypeptides can also be used such as polyasparagines, polyglutamines, polylysines, and polyarginines.

A basic, water-swellable, water-insoluble polymer generally needs to be in its free base form. In general, it is desired that the basic, water-swellable, water-insoluble polymer beneficially have at least about 50 molar percent, more beneficially at least about 70 molar percent, suitably at least about 80 molar percent, more suitably at least about 90 molar percent, and most suitably substantially about 100 molar percent of its basic functional groups in free base form. Alternatively, then, the basic, water-swellable, water-insoluble polymer should not be substantially neutralized when used in the absorbent structure of the present invention. In general, it is desired that the basic, water-swellable, water-insoluble polymer have a degree of neutralization of its basic functional groups that is beneficially less than about 50 molar percent, more beneficially less than about 30 molar percent, suitably less than about 20 molar percent, more suitably less than about 10 molar percent, and most suitably substantially about 0 molar percent.

When the first component to be used in the absorbent structure of the present invention is a basic water-swellable, water-insoluble polymer, the second component to be used in the absorbent structure of the present invention is an acidic material. As used herein, an "acidic" material is intended to refer to a material that may act as an electron acceptor and which, in an aqueous solution, exhibits a pH between about 0 to 7. Suitably, the pH is measured at about 25° C.

Examples of suitable acidic second materials include, but are not limited to, polymeric acidic materials such as polyacrylic acid, polymaleic acid, carboxymethyl cellulose, alginic acid, polyaspartic acid, and polyglutamic acid; organic acidic materials such as aliphatic and aromatic acids, such as citric acid, glutamic acid, and aspartic acid; inorganic acids such as metallic oxides, such as aluminum oxide; salts such as iron chloride, calcium chloride, and zinc chloride; and mixtures thereof. The acidic second material can generally be either a strong or a weak acid. However, the strength of the acidity of the acidic second material has been found to potentially affect the liquid absorption rate of the absorbent structure. Generally, an absorbent structure comprising a relatively stronger acidic second material will exhibit a relatively faster liquid absorption rate as compared to an absorbent structure comprising a relatively weaker acidic second material.

In general, acidic second materials useful in the absorbent structure may be either strongly or weakly acidic in nature. In general, an acidic second material that is strongly acidic will exhibit a pKa value less than about 2. In general, an acidic second material that is weakly acidic will exhibit a pKa that is greater than about 2. As such, acidic second materials useful in the absorbent structure may exhibit a broad range of pKa values, but will beneficially have a pKa between about 0 to about 12, more beneficially between about 2 to about 10, and suitably between about 3 to about 7.

In one beneficial embodiment of the present invention, the acidic second material can also suitably be a water-swellable, water-insoluble polymer. In such an embodiment, both the basic water-swellable, water-insoluble polymer and the acidic, water-swellable, water-insoluble polymeric second material can be used to contribute to the total liquid absorptive capacity of the absorbent structure, thereby potentially achieving an overall higher liquid absorptive capacity of the absorbent structure as compared to the use of an acidic second material that is not a water-swellable, water-insoluble polymer.

It may sometimes be more convenient to measure the pKa of the monomer or monomers used to prepare a polymer. Although the pKa of the monomer or monomers and the polymer prepared from such monomers may not be identical, such pKa values should be substantially similar. As such, acidic, water-swellable, water-insoluble polymers useful in the absorbent structure may be prepared from a single monomer or a combination of monomers that exhibit a broad range of pKa values, but such monomers will beneficially have a pKa between about 0 to about 12, more beneficially between about 2 to about 10, and suitably between about 3 to about 7.

The pKa of an acid represents the extent of dissociation of or, in other words, the strength of the acid and is intended herein to be measured at the conditions, such as at a specific temperature, under which the acid is being used. Suitably, the pKa is measured at about 25° C. In general, the weaker the acid, the higher the pKa value will be. The pKa values for many bases at various temperatures are well known and may be found in any of many available references, such as in the CRC Handbook of Chemistry & Physics, 75$^{th}$ Edition, edited by David R. Lide, CRC Press (1994).

Suitable acidic second materials will include functional groups that are capable of acting as acids. Such functional groups include, but are not limited to, carboxyl groups, sulfonic groups, sulphate groups, sulfite groups, and phosphate groups. Suitably, the functional groups are carboxyl groups. When the acidic second material is a water-swellable, water-insoluble polymer, the functional groups are generally attached to a crosslinked base polymer. Suitable base polymers include polyacrylamides, polyvinyl alcohols, ethylene maleic anhydride copolymer, polyvinylethers, polyacrylamido methylpropane sulfonic acid, polyacrylic acids, polyvinylpyrrolidones, polyvinylmorpholines, and copolymers of the preceding polymers. Natural based polysaccharide polymers may also be used and include carboxymethyl celluloses, carboxymethyl starches, hydroxypropyl celluloses, algins, alginates, carrageenans, acrylic grafted starches, acrylic grafted celluloses, and copolymers of the preceding polymers. Synthetic polypeptides can also be used such as polyaspartic acid and polyglutamic acid.

An acidic, water-swellable, water-insoluble polymer generally needs to be in its free acid form. In general, it is desired that the acidic, water-swellable, water-insoluble polymer beneficially have at least about 50 molar percent, more beneficially at least about 70 molar percent, suitably at least about 80 molar percent, more suitably at least about 90 molar percent, and most suitably substantially about 100 molar percent of its acidic functional groups in free acid form. Alternatively, then, the acidic, water-swellable, water-insoluble polymer should not be substantially neutralized when used in the absorbent structure of the present invention. In general, it is desired that the acidic, water-swellable, water-insoluble polymer have a degree of neutralization of its acidic functional groups that is beneficially less than about 50 molar percent, more beneficially less than about 30 molar percent, suitably less than about 20 molar percent, more suitably less than about 10 molar percent, and most suitably substantially about 0 molar percent.

The basic or acidic second material may generally be used in the absorbent structure in a variety of forms. Examples of forms that the basic or acidic second material may take include particles, flakes, fibers, films, and nonwoven structures. When the absorbent structure is used in disposable absorbent products, it is generally desired that the basic or acidic second material be in the form of discrete particles, fibers, or flakes in a fibrous matrix. When in the form of a particle, it is generally desired that the particle have a maximum cross-sectional dimension beneficially within the range from about 50 micrometers to about 2,000 micrometers, suitably within the range from about 100 micrometers to about 1,000 micrometers, and more suitably within the range from about 300 micrometers to about 600 micrometers. The combination of the acidic water-swellable, water-insoluble polymer and the basic second material, or of the basic water-swellable, water-insoluble polymer and the acidic second material, may also be in the form of bicomponent fibers, wherein one component is the acidic or basic water-swellable, water-insoluble polymer and the other component is the basic or acidic second material. Such a bicomponent fiber may be a side-by-side bicomponent fiber or a sheath-and-core bicomponent fiber. Such bicomponent fibers may be prepared by known methods, such as co-extrusion methods.

In general, the acidic water-swellable, water-insoluble polymer, substantially in its free acid form, is mixed with a basic second material in the absorbent structure in a molar ratio of the respective acidic and basic functionalities that is sufficient to provide the absorbent structure with desired absorbent and pH properties. The molar ratio of the acidic water-swellable, water-insoluble polymer to the basic second material is beneficially from about 10:1 to about 1:10, suitably from about 4:1 to about 1:4, more suitably from about 2:1 to about 1:2, and most suitably at about 1:1.

In general, the basic water-swellable, water-insoluble polymer, substantially in its free base form, is mixed with an acidic second material in the absorbent structure in a molar ratio of the respective basic and acidic functionalities that is sufficient to provide the absorbent structure with desired absorbent and pH properties. The molar ratio of the basic water-swellable, water-insoluble polymer to the acidic second material is beneficially from about 10:1 to about 1:10, suitably from about 4:1 to about 1:4, more suitably from about 2:1 to about 1:2, and most suitably at about 1:1.

In one embodiment of the present invention, the acidic or basic water-swellable, water-insoluble polymer and the basic or acidic second material may be mixed together to prepare an absorbent composition. An absorbent composition comprising the acidic or basic water-swellable, water-insoluble polymer and the basic or acidic second material suitably has the ability to absorb a liquid, herein referred to as Free Swell (FS). The method by which the Free Swell value is determined is set forth below in connection with the examples. The Free Swell values determined as set forth below and reported herein refer to the amount in grams of an aqueous solution, containing 0.9 weight percent sodium chloride, a gram of a material can absorb in about 10 hours under a negligible load of about 0.01 pound per square inch (psi). As a general rule, it is desired that an absorbent composition has a Free Swell value, for a load of about 0.01 psi, of at least about 15, beneficially of at least about 20, suitably of at least about 25, and up to about 200 grams per gram.

An absorbent composition comprising the acidic or basic water-swellable, water-insoluble polymer and the basic or acidic second material also suitably has the ability to absorb a liquid while the absorbent composition is under an external pressure or load, herein referred to as Absorbency Under Load (AUL). Synthetic polymeric materials, such as sodium polyacrylates, having a generally high ability to absorb a liquid while under a load, have been found to minimize the occurrence of gel-blocking when incorporated in absorbent products. The method by which the Absorbency Under Load is determined is set forth below in connection with the examples. The Absorbency Under Load values determined as set forth below and reported herein refer to the amount in grams of an aqueous solution, containing 0.9 weight percent sodium chloride, a gram of a material can absorb in about 10 hours under a load of about 0.3 pound per square inch (psi). As a general rule, it is desired that an absorbent composition has an Absorbency Under Load value, for a load of about 0.3 psi, of at least about 15, beneficially of at least about 20, suitably of at least about 25, and up to about 100 grams per gram.

In one embodiment of the present invention, an absorbent composition comprising the acidic or basic water-swellable, water-insoluble polymer and the basic or acidic second material suitably has the ability to relatively slowly absorb a liquid. The use of acidic, water-swellable, water-insoluble polymers that are strongly acidic, exhibiting a pKa less than about 2, or the use of basic, water-swellable, water-insoluble polymers that are strongly basic, exhibiting a pKa greater than about 12, have been found to generally result in absorbent compositions that generally do not exhibit the desired slow-rate of absorbing liquids. The use of acidic, water-swellable, water-insoluble polymers that are too weakly acidic, exhibiting a pKa greater than about 12, or the use of basic, water-swellable, water-insoluble polymers that are weakly basic, exhibiting a pKa less than about 2, have generally been found to result in absorbent compositions that generally do not exhibit the desired liquid absorbent capacity. The preparation of an absorbent composition comprising, in one embodiment, an acidic water-swellable, water-insoluble polymer and a basic second material or, in another embodiment, a basic water-swellable, water-insoluble polymer and an acidic second material, and suitably having the ability to relatively slowly absorb a liquid is described in copending U.S. patent application Ser. No.

08/759,108, filed Dec. 2, 1996, the specification of which is hereby incorporated in its entirety.

As used herein, the quantification of the rate with which an absorbent composition absorbs a liquid will be referred to as the Time to Reach 60 Percent of Free Swell Capacity value. The method by which the Time to Reach 60 Percent of Free Swell Capacity value is determined is set forth below in connection with the examples. The Time to Reach 60 Percent of Free Swell Capacity values determined as set forth below and reported herein refer to the time, in minutes, that it takes an absorbent composition to absorb about 60 percent of the absorbent composition's total absorptive capacity, as represented by the absorbent composition's Free Swell value. In one embodiment, it is desired that the absorbent composition of the present invention has a Time to Reach 60 Percent of Free Swell Capacity value of at least about 5 minutes, beneficially between about 5 minutes to about 300 minutes, more beneficially between about 10 minutes to about 200 minutes, suitably between about 20 minutes to about 100 minutes, and more suitably between about 30 minutes to about 60 minutes.

In another embodiment, an absorbent composition of the present invention suitably also has the ability to relatively slowly absorb a liquid while the absorbent composition is under an external pressure or load. As used herein, the quantification of the rate with which an absorbent composition absorbs a liquid while the absorbent composition is under an external pressure or load will be referred to as the Time to Reach 60 Percent of Absorbency Under Load Capacity value. The method by which the Time to Reach 60 Percent of Absorbency Under Load Capacity value is determined is set forth below in connection with the examples. The Time to Reach 60 Percent of Absorbency Under Load Capacity values determined as set forth below and reported herein refer to the time, in minutes, that it takes an absorbent composition to absorb about 60 percent of the absorbent composition's total absorptive capacity under an external pressure or load, as represented by the absorbent composition's Absorbency Under Load value. In such an embodiment, it is desired that the absorbent composition has a Time to Reach 60 Percent of Absorbency Under Load Capacity value of at least about 5 minutes, beneficially between about 5 minutes to about 300 minutes, more beneficially between about 10 minutes to about 200 minutes, suitably between about 20 minutes to about 100 minutes, and more suitably between about 30 minutes to about 60 minutes.

Although an absorbent structure comprising, in one embodiment, the acidic water-swellable, water-insoluble polymer and the basic second material or, in another embodiment, a basic water-swellable, water-insoluble polymer and an acidic second material, may exhibit a desired liquid absorption capacity, it has been discovered as part of the present research that if either the difference in dissociation constants between the acidic or basic water-swellable, water-insoluble polymer and the basic or acidic second material is too large or the difference in solubility or dispersibility in an aqueous solution between the acidic or basic water-swellable, water-insoluble polymer and the basic or acidic second material is too large, then a sufficiently large temporary imbalance in the number of dissociated ions from the acidic or basic water-swellable, water-insoluble polymer and the basic or acidic second material will occur and cause a temporary pH imbalance, resulting in the absorbent structure exhibiting a pH that may be undesirably too high or too low. If the pH value within the absorbent structure, particularly at or along the upper surface of the absorbent structure oriented toward the skin of the wearer or user, is allowed to reach too high of or too low of pH values, then such an absorbent structure may result in or increase the chances of a wearer or user experiencing skin irritation. Thus, it is desired that the upper surface of the absorbent structure oriented toward the skin of the wearer maintain a substantially desired and balanced pH profile while the absorbent structure is being worn or used.

In general, it is desired that the upper surface of the absorbent structure oriented toward the skin of the wearer, generally along the entire length and width of the upper surface of the absorbent structure, exhibits a pH that remains beneficially between about 3 to about 8, more beneficially between about 4 to about 7, and suitably between about 5 to about 6.

As discussed above, it has been discovered that an imbalance in the number of dissociated ions from the acidic or basic water-swellable, water-insoluble polymer and the basic or acidic second material may occur due to at least two different characteristics of the respective materials. First, too large of a difference in the dissociation constants of the acidic or basic water-swellable, water-insoluble polymer and the basic or acidic second material may result in undesirable pH values occurring within an absorbent structure. Such a situation may result, for example, from the use of a strongly acidic or basic water-swellable, water-insoluble polymer and a weakly basic or acidic second material or, alternatively, from the use of a weakly acidic or basic water-swellable, water-insoluble polymer and a strongly basic or acidic second material. In general, a strongly acidic or basic material has the capability of reaching a more complete ionization in an aqueous solution whereas a weakly acidic or basic material can generally only reach a partial ionization in an aqueous solution.

Second, too large of a difference in the solubility or dispersibility characteristics in an aqueous solution between the acidic or basic water-swellable, water-insoluble polymer and the basic or acidic second material may also result in undesirable pH values occurring within an absorbent structure. In such a situation, the more soluble or dispersible material can reach its ionization equilibrium more quickly whereas the less soluble or dispersible material will generally take a longer time to reach its ionization equilibrium.

Thus, differences in the dissociation constants as well as the solubility or dispersibility of the acidic and-basic components can result in an imbalance in pH. In order to measure or quantify this imbalance, a method to measure the ionization rate of acidic and basic components has been developed. The ionization rate of a component as described herein represents a combination of several factors such as the dissociation constant and the solubility or dispersibility value of the component, the ionic content of a liquid in which the component is placed, and other conditions of use. By measuring the ionization rate of a component, it has been found possible to device methods that would enable the imbalance in pH in an absorbent structure to be minimized and brought within the generally acceptable range for skin-wellness. Various physical approaches that do not require additional chemical species such as buffering agents can be used to achieve a balanced pH on the surface of an absorbent structure. The following are examples of some of the physical approaches that could be used to overcome the problem of maintaining the pH within a desired range at the surface of an absorbent structure.

One method of attaining a balanced pH profile is to balance the ionization rates of the acidic and basic components by using the acidic and basic components with an appropriate particle size range. The particle size of a component is generally inversely related to surface area of the component. As such, using a smaller particle size for a component with a relatively slower ionization rate will generally expose a larger surface area of the component to a liquid. As dissolution and ionization of a component occurs only when the component contacts a liquid, providing a larger surface area over which this contact with liquid can be made generally ensures a faster ionization rate for the component. In this approach, the particle size for a component with a relatively faster ionization rate would be relatively larger as compared to the particle size of a component with a relatively slower ionization rate. By carefully selecting the particle size of the acidic and basic components to be used in an absorbent structure, this approach enables the ionization rates of the acidic and basic components to be effectively matched, thereby generally resulting in a balanced pH profile, particularly on the upper surface of an absorbent structure. Other approaches to effectively control the surface area of the components can also be used as, for example, by using components having different shapes or morphologies.

Another approach that has been found to effectively balance the ionization rates of different components is to coat or encapsulate another substance onto the surface of the acidic and/or basic components. By coating or encapsulating a component, the ionization rate of the component can generally be slowed down due to the diffusion barrier created by the coating or encapsulating material. For example, this approach can be used to coat or encapsulate a component having a relatively faster ionization rate in order to make such a component compatible with a component having a relatively slower ionization rate. In one embodiment of this approach, the component with the relatively slower ionization rate could be used as the coating or encapsulating material onto the component with the relatively faster ionization rate.

Yet another approach that has been found is the physical separation of the acidic and basic components so as to ensure that the pH on the surface of an absorbent structure remains within a desired range. Examples of this approach could include, but are not limited to, using a barrier material to separate the components or zoning the components in a layered structure. In general, this approach ensures strategic placement of the components so that the ions from the component with the relatively faster ionization rate require a longer time to reach the upper surface of an absorbent structure and the ions from the component with the relatively slower ionization rate requires a shorter time. This ensures that the pH at the upper surface of an absorbent structure is maintained within a desired range.

Still another approach that has been found is the use of an acidic component which is comprised of a mixture of acidic materials having different ionization rates. For example, a mixture of polyacrylic acid particles with different degrees of neutralization could be used such that the resulting ionization rate for this mixture effectively matches the ionization rate of the basic second material being used. This approach could also be achieved by using materials with a shell-core structure which has different degrees of neutralization in the shell and the core. A similar approach can also be applied for the basic component.

In one embodiment of the present invention, a third component is used in the absorbent structure of the present invention wherein the third component is a buffering agent. As used herein, the term "buffering agent" is intended to represent a chemical material or materials, or the corresponding acid or base of such material or materials, that exhibits a pKa between about 2 to about 10. A buffering agent, when in an aqueous solution, generally results in such solution exhibiting only slight pH changes on the addition of an acid or a base to the solution. Such a buffering agent therefore minimizes changes in the hydrogen ion concentration in an aqueous solution which would otherwise tend to occur as a result of an imbalance in the ionization of any acid or base present in the aqueous solution.

In the present invention, the selection of an effective buffering agent is generally dependent upon the strength and solubility of each of the acidic or basic water-swellable, water-insoluble polymer and the basic or acidic second material being used in an absorbent structure. For example, when the acidic water-swellable, water-insoluble polymer is weakly acidic and the basic second material is strongly basic but is either soluble or insoluble, then the buffering agent will generally need to be an acidic buffering agent. When the acidic water-swellable, water-insoluble polymer is weakly acidic and the basic second material is weakly basic and is soluble, then the buffering agent will generally need to be an acidic buffering agent. When the acidic water-swellable, water-insoluble polymer is strongly acidic and the basic second material is weakly basic and is insoluble, then the buffering agent will generally need to be a basic buffering agent. When the basic water-swellable, water-insoluble polymer is weakly basic and the acidic second material is strongly acidic but is either soluble or insoluble, then the buffering agent will generally need to be a basic buffering agent. When the basic water-swellable, water-insoluble polymer is weakly basic and the acidic second material is weakly acidic and is soluble, then the buffering agent will generally need to be a basic buffering agent. When the basic water-swellable, water-insoluble polymer is strongly basic and the acidic second material is weakly acidic and is insoluble, then the buffering agent will generally need to be an acidic buffering agent.

When a single acid or base is used as a buffering agent, the range of the buffering effect of such a buffering agent is generally approximately one pH unit on either side of the pKa of the buffering agent. For example, citric acid has a $pKa_1$ of about 3.2 and generally results in a buffering solution having a pH range of between about 2 to about 4.5. Ammonia has a pKa of about 9.2 and generally results in a buffering solution having a pH range of between about 8.2 to about 10.2. When there are two or more acidic or basic groups per molecule, or a mixture of several buffering agents is used, the pH range of the buffering solution is generally larger. For example, a mixture of citric acid and dibasic sodium phosphate results in a buffering agent solution having a pH range of between about 2.2 to about 8.0. As another example, a mixture of monobasic potassium phosphate and dibasic sodium phosphate results in a buffering agent solution having a pH range of between about 6.1 to about 7.5. As another example, a mixture of sodium hydroxide and dibasic sodium phosphate results in a buffering agent solution having a pH range of between about 11.0 to about 12.0.

When an acidic buffering agent is desired to be used in the present invention, suitable buffering agents are generally acids, or the salts of such acids, having a pKa between about 2 to about 7. Such acids include, but are not limited to aspartic acid (having a $pKa_1$ of about 3.86), ascorbic acid (having a $pKa_1$ of about 4.10), chloroacetic acid (having a pKa of about 2.85), β-chlorobutyric acid (having a pKa of about 4.05), cis-cinnamic acid (having a pKa of about 3.89), citric acid (having a $pKa_1$ of about 3.14), fumaric acid (having a $pKa_1$ of about 3.03), glutaramic acid (having a pKa of about 4.60), glutaric acid (having a $pKa_1$ of about 4.31), itaconic acid (having a $pKa_1$ of about 3.85), lactic acid (having a pKa of about 3.08), malic acid (having a $pKa_1$ of about 3.40), malonic acid (having a $pKa_1$ of about 2.83), o-phthalic acid (having a $pKa_1$ of about 2.89), succinic acid (having a $pKa_1$ of about 4.16), α-tataric acid (having a $pKa_1$ of about 2.89), and phosphoric acid (having a $pKa_1$ of about 2.12).

When a basic buffering agent is desired to be used in the present invention, suitable buffering agents are generally bases, or the salts of such bases, having a pKa between about 5 to about 10. Such bases include, but are not limited to α-alanine (having a pKa of about 9.87), allantoin (having a $pKa_1$ of about 8.96), cysteine (having a pKa of about 7.85), cystine (having a pKa of about 7.85), dimethylglycine (having a pKa of about 9.89), histidine (having a pKa of about 9.17), glycine (having a pKa of about 9.78), chitosan (having a pKa of about 7), N-(2-acetamido)-2-iminodiacetic acid (having a pKa of about 6.8), tris(hydroxymethyl)aminomethane (having a pKa of about 8.1), theobromine (having a pKa of about 7.89), and tyrosine (having a pKa of about 8.40).

The buffering agent may generally be used in the absorbent structure in a variety of forms. Examples of forms that the buffering agent may take include particles, flakes, fibers, films, and nonwoven structures. When the absorbent structure is used in disposable absorbent products, it is generally desired that the buffering agent be in the form of discrete particles, fibers, or flakes in a fibrous matrix. When in the form of a particle, it is generally desired that the particle have a maximum cross-sectional dimension beneficially within the range from about 50 micrometers to about 2,000 micrometers, suitably within the range from about 100 micrometers to about 1,000 micrometers, and more suitably within the range from about 300 micrometers to about 600 micrometers.

The amount of buffering agent used in the absorbent structure of the present invention is generally dependent on a variety of factors including the strength of the acidity or basicity of the acidic or basic water-swellable, water-insoluble polymer, the strength of the basicity or acidity of the basic or acidic second material, the relative solubilities of each of the acidic or basic water-swellable, water-insoluble polymer and the basic or acidic second material, the pKa of the buffering agent used, and the pH range desired to be maintained within the absorbent structure. In general, the amount of buffering agent used in the absorbent structure is such that the molar ratio between the acidic or basic water-swellable, water-insoluble polymer and the buffering agent is beneficially between about 50:1 to about 2:1, more beneficially between about 40:1 to about 4:1, suitably between about 30:1 to about 6:1, and more suitably between about 20:1 to about 10:1. In general, the amount of buffering agent used in the absorbent structure is such that the molar ratio between the basic or acidic second material and the buffering agent is beneficially between about 50:1 to about 2:1, more beneficially between about 40:1 to about 4:1, suitably between about 30:1 to about 6:1, and more suitably between about 20:1 to about 10:1.

In one embodiment of the present invention, the buffering agent used can be the same material used as either the acidic water-swellable, water-insoluble polymer or the basic second material when the acidic water-swellable, water-insoluble polymer has a pKa between about 2 to about 7 and an acidic buffering agent is required, or when the basic second material has a pKa between about 5 to about 10 and a basic buffering agent is required. For example, when polyacrylic acid is used as the acidic water-swellable, water-insoluble polymer and sodium hydrogen carbonate is used as the basic second material, an acidic buffering agent, such as citric acid, is generally required in order to maintain the pH profile in a desirable range because sodium hydrogen carbonate is more soluble than the polyacrylic acid. However, polyacrylic acid can also be used as an acidic buffering agent since the polyacrylic acid has a pKa of about 4.25. Another example is wherein polyacrylamide methylpropane sulfonic acid is used as the acidic water-swellable, water-insoluble polymer and chitosan is used as the basic second material. In this example, a basic buffering agent, such as sodium hydrogen carbonate, is generally required in order to maintain the pH profile in a desirable range because the polyacrylamide methylpropane sulfonic acid is a strongly acidic polymer and the chitosan is a weakly basic polymer. However, chitosan can also be used as a basic buffering agent since the chitosan has a pKa of about 7.

In another embodiment of the present invention, the buffering agent used can be the same material used as either the basic water-swellable, water-insoluble polymer or the acidic second material when the basic water-swellable, water-insoluble polymer has a pKa between about 7 to about 12 and a basic buffering agent is required, or when the acidic second material has a pKa between about 4 to about 9 and an acidic buffering agent is required. For example, when chitosan is used as the basic water-swellable, water-insoluble polymer and citric acid is used as the acidic second material, a basic buffering agent, such as sodium hydrogen carbonate, is generally required in order to maintain the pH profile in a desirable range because citric acid is more soluble than the chitosan. However, chitosan can also be used as a basic buffering agent since the chitosan has a pKa of about 7. Another example is wherein crosslinked polydiallyl dimethyl ammonium hydroxide is used as the basic water-swellable, water-insoluble polymer and crosslinked polyacrylic acid is used as the acidic second material. In this example, an acidic buffering agent, such as citric acid, is generally required in order to maintain the pH profile in a desirable range because the polydiallyl dimethyl ammonium hydroxide is a strongly basic polymer and the polyacrylic acid is a weakly acidic polymer. However, polyacrylic acid can also be used as an acidic buffering agent since the polyacrylic acid has a pKa of about 4.25.

In one embodiment of the present invention, it is desired that the acidic or basic water-swellable, water-insoluble polymer, the basic or acidic second material, and, optionally, the buffering agent be prepared as an absorbent composition that may be incorporated into an absorbent structure. Such an absorbent composition may be prepared by a simple process. In general, the method of making such an absorbent composition comprises the step of mixing together the acidic or basic water-swellable, water-insoluble polymer, the basic or acidic second material, and, optionally, the buffering agent.

When the second basic material is water-insoluble, such as crosslinked polydiallyl dimethyl ammonium hydroxide, homogeneous mixing of the acidic water-swellable, water-insoluble polymer with the basic second material is generally required for promoting uniform ion exchanging and achieving a desirable pH profile. However, when the second basic material is water-soluble, such as sodium hydrogen carbonate, homogeneous mixing of the acidic water-swellable, water-insoluble polymer with the basic second material is generally not required due to the mobility of the basic second material when the absorbent structure is insulted with a liquid. The basic second material can dissolve into and flow with the liquid to reach the acidic water-swellable, water-insoluble polymer.

When the acidic second material is water-insoluble, such as crosslinked polyacrylic acid, homogeneous mixing of the basic water-swellable, water-insoluble polymer with the acidic second material is generally required for promoting uniform ion exchanging and achieving a desirable pH profile. However, when the second acidic material is water-soluble, such as citric acid, homogeneous mixing of the basic water-swellable, water-insoluble polymer with the acidic second material is generally not required due to the mobility of the acidic second material when the absorbent structure is insulted with a liquid. The acidic second material can dissolve into and flow with the liquid to reach the basic water-swellable, water-insoluble polymer.

Mixtures of the components should generally be prepared under conditions that are sufficient for the acidic or basic water-swellable, water-insoluble polymer, the basic or acidic second material, and, optionally, the buffering agent to be effectively mixed together. Such mixtures will beneficially be agitated, stirred, or otherwise blended to effectively mix the acidic or basic water-swellable, water-insoluble polymer, the basic or acidic second material, and, optionally, the buffering agent such that an essentially uniform mixture is formed. Equipment for achieving such agitation, stirring, or blending are well known in the art and include simple blenders and mixers and suitable forming equipment.

In another embodiment of the present invention, the buffering agent may be used as or contained in an essentially separate layer or component of the absorbent structure such as, for example, a surge layer or a tissue sheet that is located near the upper surface of the absorbent structure. Such an embodiment may be effective in reducing the amount of buffering agent that is needed in the absorbent structure in order to achieve the desired property of maintaining a substantially desired and balanced pH profile on or along the upper surface of the absorbent structure. In addition, substantially separating the acidic or basic water-swellable, water-insoluble polymer and the buffering agent may help to enhance the total liquid absorbing capacity of the absorbent structure due to being able to maintain the acidic or basic water-swellable, water-insoluble polymer at a relatively higher pH which may increase the liquid absorbing capacity of the acidic or basic water-swellable, water-insoluble polymer.

While the principal components of the absorbent structure have been described in the foregoing, such an absorbent structure is not limited thereto and can include other components not adversely effecting the absorbent structure or the use of the absorbent structure having the desired absorbent and pH properties. Exemplary materials which could be used as additional components would include, without limitation, pigments, antioxidants, stabilizers, surfactants, waxes, flow promoters, solid solvents, particulates, and materials added to enhance the processability of the absorbent structure.

The absorbent structure of the present invention is suitable for use in disposable absorbent products such as personal care products, such as diapers, training pants, baby wipes, feminine care products, adult incontinent products; medical products, such as wound dressings or surgical capes or drapes; and tissue products. In one embodiment of the present invention, a disposable absorbent product is provided, which disposable absorbent product comprises a liquid-permeable topsheet, a backsheet attached to the topsheet, and an absorbent structure positioned between the topsheet and the backsheet wherein the absorbent structure comprises the acidic water-swellable, water-insoluble polymer, the basic second material, and the buffering agent, and wherein the absorbent structure exhibits desired absorbent and pH properties.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

The acidic or basic water-swellable, water-insoluble polymer, the basic or acidic second material, and, optionally, the buffering agent are typically present in an absorbent structure in conjunction with a fibrous matrix. A fibrous matrix may take the form of, for example, a batt of comminuted wood pulp fluff, a tissue layer, a hydroentangled pulp sheet, or a mechanically softened pulp sheet. Suitably, the fibrous matrix is formed so as to constrain or entrap the acidic or basic water-swellable, water-insoluble polymer, the basic or acidic second material, and, optionally, the buffering agent within, or onto, its structure. The acidic or basic water-swellable, water-insoluble polymer, the basic or acidic second material, and, optionally, the buffering agent may be incorporated into or onto the fibrous matrix either during or after the formation of the general form of the fibrous matrix. A fibrous matrix useful in the present invention may be formed by an air-laying process or a wet-laid process, or by essentially any other process known to those skilled in the art for forming a fibrous matrix. The fibrous matrix may be formed from either natural fibers or synthetic fibers or a mixture of both natural and synthetic fibers.

The acidic or basic water-swellable, water-insoluble polymer, the basic or acidic second material, and, optionally, the buffering agent are typically present in an absorbent structure or disposable absorbent product of the present invention in an amount effective to result in the absorbent structure or disposable absorbent product being able to absorb a desired amount of liquid and exhibit desired pH properties. The acidic or basic water-swellable, water-insoluble polymer, the basic or acidic second material, and, optionally, the buffering agent are beneficially present in an absorbent structure in an amount of from about 1 to about 100 weight percent, more beneficially in an amount of from about 5 to about 95 weight percent, suitably in an amount of from about 10 to about 90 weight percent, and more suitably of from about 30 to about 70 weight percent, based on the total weight of the absorbent structure.

It is generally desired that the absorbent structure of the present invention has the ability to absorb a desired quantity of liquid, such as urine, blood, menses, synthetic urine, or an aqueous solution comprising 0.9 weight percent sodium chloride. In one embodiment of the present invention, it is desired that an absorbent structure has the ability to absorb a quantity of liquid as quantified by a Wicking Capacity value. As used herein, the Wicking Capacity value, reported in grams per gram, refers to the amount of an aqueous solution, containing 0.9 weight percent sodium chloride, a gram of an absorbent structure can absorb in about 6 hours as measured by the method described in the Test Methods section herein.

It is generally desired that an absorbent structure exhibit a Wicking Capacity value that is beneficially at least about 5 grams per gram, more beneficially at least about 10 grams per gram, suitably at least about 15 grams per gram, more suitably at least about 20 grams per gram, and up to about 40 grams per gram.

Test Methods

Free Swell Capacity and Time to Reach 60 Percent of Free Swell Capacity

The Free Swell Capacity (FS) is a test which measures the amount in grams of an aqueous solution, containing 0.9 weight percent sodium chloride, a gram of a material can absorb in 10 hours under a negligible applied load or restraining force, such as of about 0.01 pound per square inch.

Referring to FIG. 1, the apparatus and method for determining the Free Swell and the Absorbency Under Load will be described. Shown is a perspective view of the apparatus in position during a test. Shown is a laboratory jack 1 having an adjustable knob 2 for raising and lowering the platform 3. A laboratory stand 4 supports a spring 5 connected to a modified thickness meter probe 6, which passes through the housing 7 of the meter, which is rigidly supported by the laboratory stand. A plastic sample cup 8, which contains the superabsorbent material sample to be tested, has a liquid-permeable bottom and rests within a Petri dish 9 which contains the saline solution to be absorbed. For the determination of Absorbency Under Load values only, a weight 10 rests on top of a spacer disc (not visible) resting on top of the superabsorbent material sample (not visible).

The sample cup consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe, located on the top of the meter housing, is also removed to enable attachment of the probe to the suspension spring 5 (available from McMaster-Carr Supply Co., Chicago, Ill., Item No. 9640K41), which serves to counter or reduce the downward force of the probe to about 1 gram±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of an absorbent material sample, which has typically been sieved to a particle size between 300 and 600 microns, is placed into the sample cup. The sample is then covered with a plastic spacer disc, weighing 4.4 grams and having a diameter of about 0.995 inch, which serves to protect the sample from being disturbed during the test and also to uniformly apply a load on the entire sample. The sample cup, with material sample and spacer disc, is then weighed to obtain its dry weight. The sample cup is placed in the Petri dish on the platform and the laboratory jack raised up until the top side of the plastic spacer disc contacts the tip of the probe. The meter is zeroed. A sufficient amount of saline solution is added to the Petri dish (50–100 milliliters) to begin the test. The distance the plastic spacer disc is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after about 10 hours is the Free Swell value expressed as grams saline solution absorbed per gram of absorbent. If desired, the readings of the modified thickness meter can be continuously inputted to a computer (Mitutoyo Digimatic Miniprocessor DP-2 DX) to make the calculations and provide Free Swell readings. As a cross-check, the Free Swell can also be determined by determining the weight difference between the sample cup before and after the test, the weight difference being the amount of solution absorbed by the sample.

From the continuous monitoring of the Free Swell values provided by the computer, the Time to Reach 60 Percent of Free Swell Capacity is readily determined.

Absorbency Under Load Capacity and Time to Reach 60 Percent of Absorbency Under Load Capacity The Absorbency Under Load (AUL) is a test which measures the amount in grams of an aqueous solution, containing 0.9 weight percent sodium chloride, a gram of a material can absorb in 10 hours under an applied load or restraining force of about 0.3 pound per square inch. The procedure for measuring the Absorbency Under Load value of an absorbent composition is essentially identical to the procedure for measuring the Free Swell values, except that a 100 gram weight is placed on top of the plastic spacer disc, thereby applying a load of about 0.3 pound per square inch onto the absorbent composition as it absorbs the saline solution. From the continuous monitoring of the Absorbency Under Load values provided by the computer, the Time to Reach 60 Percent of Absorbency Under Load Capacity is readily determined.

Wicking Capacity and pH Range Measurements

Figure 2:
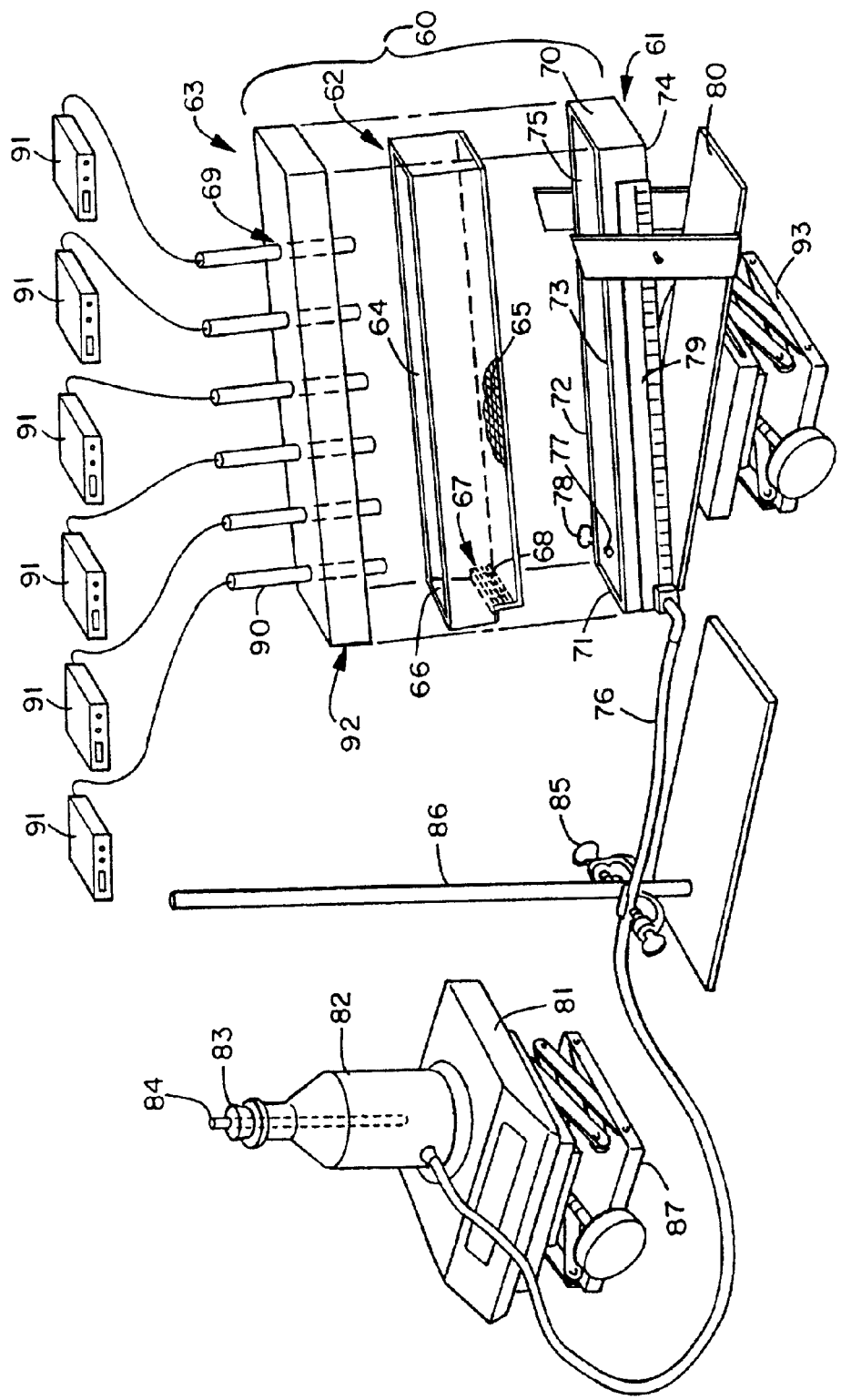
FIG. 2 is an illustration of the equipment employed in determining the Wicking Capacity of an absorbent structure as well as the pH values along the upper surface of an absorbent structure.

Referring to the attached FIG. 2, the apparatus and method for determining the wicking capacity and pH profiles will be further described.

FIG. 2 is an exploded perspective view of the apparatus used for carrying out the wicking capacity and pH profile measurement. FIG. 2 illustrates the test container 60 comprising a holding chamber 61, a testing chamber 62, and a cover 63. Testing chamber 62 is a rectangular chamber 5.08 cm (2 inches) wide, 35.56 cm (14 inches) long, and 4.445 cm (1.75 inches) deep (internal dimensions). The testing chamber 62 is suitably formed from a clear material such as an acrylic resin commercially available under the designation LUCITE™ (0.635 cm [0.25 inch] thick). The top 64 of testing chamber 62 is open. The bottom 65 of testing chamber 62 is formed from 100 mesh stainless steel screen. The metal screen is adhered to the material forming the sides and ends of testing chamber 62. The longitudinal end 66 of the test chamber 62 is formed by a piece of acrylic resin which is dimensioned such that the testing chamber 62 defines a 5.08 cm (2 inches) wide by 0.9525 cm (0.375 inch) deep opening 67 is covered with a 100 mesh stainless metal screen 68. The mesh screen 68 is suitably adhered to the acrylic resin forming test chamber 62 around the periphery of opening 67. The bottom 65 and end screen 68 are adhered at their juncture or are formed as a single, integral piece.

The holding chamber 61 comprises longitudinal ends 70, 71, lateral sides 72, 73, and bottom 74. Holding chamber 61 is suitably formed from a clear resin such as acrylic resin (0.635 cm [0.25 inch] thick). Longitudinal ends 70, 71, lateral sides 72, 73, and bottom 74 of holding chamber 61 define a top opening 75. When the testing chamber 62 is formed from 0.635 cm (0.25 inch) thick acrylic resin, the holding chamber 61 is dimensioned to form a chamber 6.35 cm (2.5 inches) wide, 36.83 cm (14.5 inches) long and 5.08 cm (2 inches) deep (internal dimensions). In any event, holding chamber 61 is internally dimensioned so that testing chamber 62 can just pass into, and snugly fit within, the interior of holding chamber 61.

Cover 63 is similarly formed from a clear acrylic resin and is dimensioned to cover the top opening 75 of the holding chamber 61 when the testing chamber 62 is present therein. Cover 63 defines an interior chamber 6.35 cm (2.5 inches) wide, 36.83 cm (14.5 inches) long and 1.4288 cm (0.5625 inch) deep. On the top of cover 63, there are six holes 69 dimensioned to hold pH electrodes. Internal diameter of the hole 69 is about 1.20 cm (0.472 inch) which allows the electrode pass through, and snugly fit within, the hole 69 of cover 63. The holes 69 are located longitudinally at 0.6, 5, 10, 15, 20, and 25 cm from longitudinal end 92.

An absorbent structure sample having a basis weight of about 500 grams per square inch and a density of about 0.2 g/cm$^3$, is cut into a rectangular shape with a dimension of 4.92 cm (1.94 inches) width and 34.93 cm (13.75 inches) length by a textile saw, available from Eastman Machine Company in Buffalo, N.Y., under the designation Chickadee II Rotary Shear, Type D-2, 110 volt textile saw. The textile saw creates smooth edges without changing the edge density of the absorbent structure sample. The cut piece of the absorbent structure sample is then placed on the mesh screen forming bottom 65 of the testing chamber 62.

ORION Gel-Filled Combination Electrodes model 91-35, which are available from ORION Research Inc., are used for this testing. The tip of the pH electrode 90 is covered by a cap which protects the electrode 90 and keeps it from drying out. The cap is part of the electrodes obtained from the manufacturer. The cap has to be removed before testing and saved for storage. The tip of the electrode 90 sits on the surface of the absorbent structure sample in the way that the electrodes is perpendicular to the surface of the absorbent structure sample. No additional pressure other than the weight of the electrode 90 is needed to ensure a good contact and non-disrupted surface. The electrodes 90 are separately connected to respective pH meter 91 (ORION Benchtop pH/ISE Meter, model 710A, also available from ORION Research Inc.). The meter/electrode system is calibrated with three buffers (pH=4.01, 7.00, and 10.00, available from VWR Scientific Co. with catalogue number 34170-127, 34170-130, and 34170-133 respectively) prior to the testing.

The test container 60 is then placed on inclined base 80 which is configured such that the bottom 74 of holding chamber 61 forms an incline angle of 30 degrees above horizontal such that the horizontal end 70 is higher than the horizontal end 71. The inclined base 80 in turn rests on laboratory jack 93. A reservoir for liquid is provided comprising an aspirator bottle 82 including a rubber stopper 83 and an aspirator tube 84. The rubber stopper 83 has to be tightly inserted into the aspirator bottle 82 to prevent air from leaking. The aspirator bottle 82 is connected by supply tube 76 to holding chamber 61. Supply tube 76 is supported by clamp 85 which is attached to a laboratory stand 86 in order to minimize the effect of movement of supply tube 76 on electronic balance (scale) 81 during testing. The aspirator bottle rests on an electronic balance 81. The electronic balance 81 in turn rests on laboratory jack 87. The aspirator bottle is filled with an aqueous solution containing 0.9 weight percent sodium chloride. The saline solution in aspirator bottle 82 is colored with FD & C blue dye No. 1 to facilitate/enhance measurement readings.

To start the testing procedure, testing chamber 62 and cover 63 are removed from holding chamber 61 which remains in place on incline base 80. The aspirator bottle is raised on laboratory jack 87 to an arbitrary height. The inclined base 80 is raised on laboratory jack 93 until the saline solution contained in aspirator bottle 82 fills the lower end (about 0.64 cm (about 0.25 inch) or holding chamber 61 to a 0.635 cm (0.25 inch) depth at its deepest point. At this point, the testing chamber 62 is placed in the holding chamber 61 but is held out of contact with the saline solution present in holding chamber 61 by screw 78. Specifically, screw 78 is passed through threaded opening 77 until it contacts the side of test chamber 62. The force exerted by screw 78 presses test chamber 62 against holding chamber 61 and prevents the test chamber 62 from completely entering holding chamber 61. Cover 63 is then placed on holding chamber 61. Six pH probes 90 are inserted through the holes 69 of cover 63 until they contact the surface of the composite. The pH meters 91 are set in the measurement mode. Balance 81 is then zeroed, and the bottom end of screen 68 is lowered into the saline solution by releasing the force exerted by screw 78. The junction of screen 68 and bottom 65, and the absorbent structure sample located generally thereat, contact the saline solution. The saline solution is fed at a constant hydrostatic head from the aspirator bottle 82 into the lower end of holding chamber 61. The progress of the saline solution in centimeters, the increase in weight (as registered by balance 81), and the readings on pH meters 91 (only those electrodes contacting saturated absorbent structure sample display pH values, otherwise no values are obtained), as a function of time, are recorded for a period of six hours with, generally, periodic measurements being recorded as, for example, at two minute intervals for the first 5 readings and then ten minute intervals for the rest of the readings. The Wicking Capacity value is defined and normalized as the increase in liquid weight registered by balance 81 at the end of the testing divided by the dry weight of the absorbent structure. The pH range is presented as the minimum and maximum pH values obtained during the testing period by any pH meters 91.

Ionization Rate

The Ionization Rate test method measures the initial Ionization Rate of an ionizable material in 0.9 weight percent sodium chloride aqueous solution.

A stock 0.9 weight percent sodium chloride aqueous solution is prepared by dissolving 67.5 grams of sodium chloride, available from Aldrich Chemical Company in Milwaukee, Wis. with catalog number 22,351-4, under the Chemical Abstract Service Registry number [7647-14-5], and with a chemical purity greater than 99 percent, in 7.5 liters of ultrapure water contained in a 18.7 liter plastic utility bucket. The ultrapure water is obtained by filtering distilled water through a filtering system, available from Millipore Corporation of Bedford, Mass., under the designation Milli-Q Reagent Water System. A Nuova II stir plate, available from Thermolyne Corporation of Dubuque, Iowa, and a 7 cm long magnetic stir bar is used to thoroughly mix and dissolve the sodium chloride in the ultrapure water. The 7.5 liter of stock 0.9 weight percentage aqueous solution of sodium chloride is stirred for about 72 hours. A cover is placed on top of the 18.7 liter plastic utility bucket during the 72 hour stirring time, so as to limit dust or other particulate contamination of the solution, leaving only a very small opening for air exchange. This will allow the stock saline solution to equilibrate with the carbon dioxide in the air, thus stabilizing the pH level of the stock saline solution.

Figure 3:
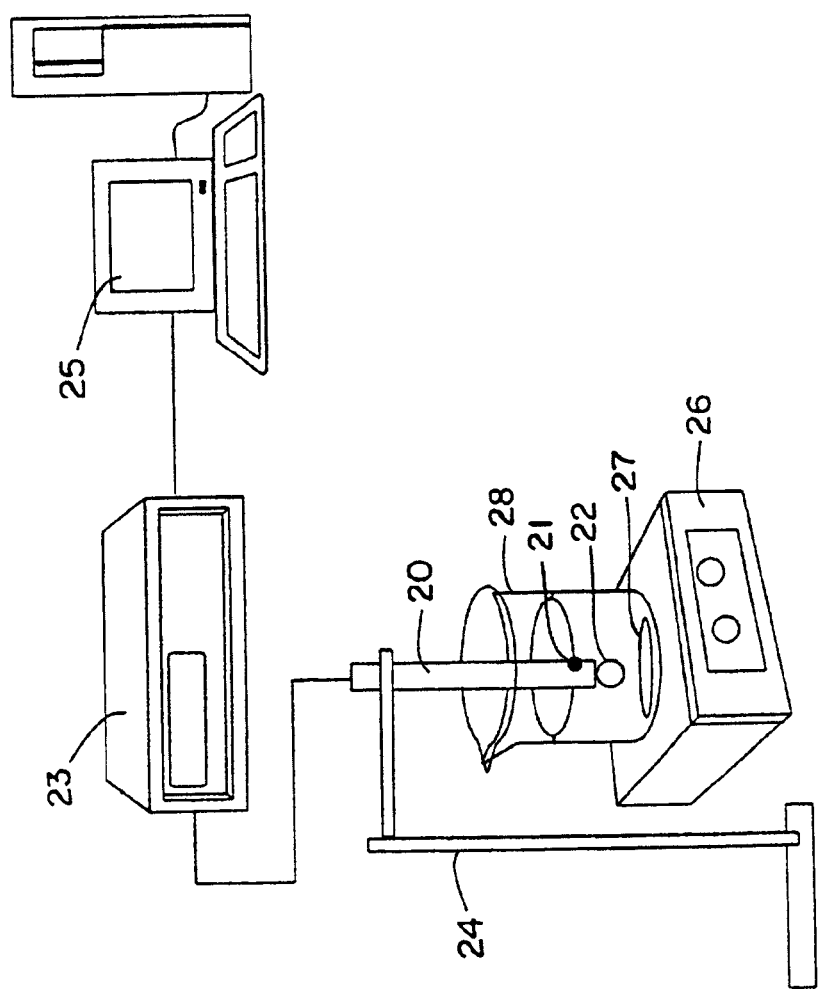
FIG. 3 is an illustration of the equipment employed in determining the Ionization Rate of a material.

An ORION Ross Glass Combination pH electrode model 8202BN, which is available from ORION Research Inc. in Boston, Mass., is used in this testing. Referring to FIG. 3, the tip of the pH electrode 20 is covered by a cap which protects the electrode 20 and keeps it from drying out. The cap is part of the electrode obtained from the manufacturer. The electrode 20 is connected to the pH meter 23 (ORION Benchtop pH/ISE Meter, model 710A, also available from ORION Research Inc.). The pH meter 23 is interfaced to a computer 25 (such as a Compaq Portable 386 available from Compaq Computer) for acquiring pH values versus time. The meter/electrode system is calibrated with three buffers (pH=4.01, 7.00, and 10.00, available from VWR Scientific Co. with catalog numbers 34170-127, 34170-130, and 34170-133 respectively) prior to the testing. The pH electrode 20 is suspended vertically in a solution being measured by the pH electrode holder 24. Both the pH electrode reference junction 21 and the pH sensing bulb 22 must be totally immersed in the solution being measured in order to function properly.

The computer 25 is turned on and the data acquisition software is started. The sample identification is entered into the program and the program is set to record data every 5 seconds for a suitable length of time.

To start the testing procedure, 200 grams of the stock 0.9 weight percent sodium chloride aqueous solution is measured into a 250 ml glass beaker 28 using an electronic balance (scale) available from Sartorius Corporation in Bohemia, N.Y. A mass of about 2 grams of the testing material is weighed using the same electronic balance. The glass beaker 28 containing the 200 grams of stock saline solution is placed on the Nuova II stir plate 26 and the magnetic stir bar 27, about 3.18 cm (1.25 inch) long, is placed into the beaker. The Nuova II stir plate 26 is turned on and set to a stir rate setting of 8. The pH electrode 20 is immersed into the solution and suspended in the center of the beaker. The tip of the pH sensing bulb 22 is immersed about 3 cm (1.18 inch) into the solution. The pH meter is set in the measurement mode. When the pH value of the stock saline solution has not changed within 5 minutes, the ionization rate measurement is ready to begin.

The measurement of the ionization rate begins with the data acquisition software ready to acquire data and the stock saline solution being continuously stirred at a stir rate setting of 8. Then two grams of the testing material is poured into the beaker 28 of stock saline solution. The data acquisition software records the pH values of the solution every 5 seconds. The test is conducted for at least 10 minutes. A longer test time is needed for materials with weaker ionic strength and/or lower solubility in saline. The test can be stopped when the final pH value has stabilized for at least 2 minutes. The pH electrode 20 is carefully removed from the solution and it is cleaned with distilled water. The glass beaker 28 is washed with distilled water and dried cleanly. The test procedure is repeated for at least three replicates per testing material. The Ionization Rate for each testing material will be an average of at least three replicates.

The Ionization Rate of a material is defined as the change of the pH value as measured at 5 seconds relative to the full range of pH upon full ionization as a function of time.

The Ionization Rate is calculated using the following equation:

$$\text{Ionization Rate} = \frac{\left|\frac{pH_5 - pH_0}{pH_m - pH_0}\right|}{5 \text{ sec}} \cdot \frac{60 \text{ sec}}{\text{min}} = 12 \cdot \left|\frac{pH_5 - pH_0}{pH_m - pH_0}\right| \text{ min}^{-1}$$

where $pH_0$=pH value of the stock saline solution before the testing material is added (0 sec)

$pH_5$=pH value at 5 seconds $pH_m$=For acidic materials, $pH_m$ represents the minimum pH value recorded during the evaluation. For basic materials, $pH_m$ represents the maximum pH value recorded during the evaluation.

EXAMPLES

For use in the following examples, the following component materials were obtained or prepared.

a. Commercial Polyacrylate Superabsorbent (Component 1)

As a control material, a commercial sodium polyacrylate superabsorbent, designated as FAVOR® 880 superabsorbent polymer, was obtained from Stockhausen, Inc. of Greensboro, N.C. This superabsorbent has a degree of neutralization of about 70 mole percent. The superabsorbent was sieved and the 300 to 600 micrometers particle size range was used for further evaluation. The FAVOR® 880 superabsorbent polymer had a Free Swell value of about 40 grams per gram and an Absorbency Under Load value of about 30 grams per gram.

b. Polyacrylic Acid Gel (Component 2)

Into a 10 gallon jacketed reactor, equipped with an agitator and containing 24 kg of distilled water, 6 kg of acrylic acid, 10 grams of potassium persulfate ($K_2S_2O_8$), and 24 grams of N,N'-methylenebisacrylamide, all available from Aldrich Chemical Company, were added and mixed at room temperature to form a completely dissolved solution. The reactor was then heated to 60° C. for at least four hours. The agitator was on continuously. The polyacrylic acid gel formed was cut into less than 1 inch cubes and dried in a ventilated oven at 60° C. for at least two days. The completely dried polyacrylic acid polymer was ground into particulate by a commercial grinder (Model: C. W. Brabender Granu-Grinder) and sieved using a Sweco Separator (24 inch Model), with four different particle size ranges (150 to 300 micrometers, 300 to 600 micrometers, 600 to 850 micrometers, and 850 to 1190 micrometers) being used for further evaluation, designated as Components 2a, 2b, 2c, and 2d respectively. The polyacrylic acid polymers had a Free Swell value of about 9 grams per gram and an Absorbency Under Load value of about 6 grams per gram.

c. Basic Second Material or Buffering Agent (Component 3)

Granular sodium hydrogen carbonate ($NaHCO_3$), available from Aldrich Chemical Company, was obtained and sieved, with the 300 to 600 micrometers particle size range being used for further evaluation.

d. Basic Second Material (Component 4)

Granular sodium carbonate ($Na_2CO_3$), available from Aldrich Chemical Company, was obtained and sieved, with the 300 to 600 micrometers particle size range being used for further evaluation.

e. Acidic Second Material or Buffering Agent (Component 5)

Granular anhydrous citric acid ($HOOCCH_2C(OH)(COOH)CH_2COOH$), available from Archer Daniels Midland Company, was obtained and sieved, with the 300 to 600 micrometers, 600 to 850 micrometers, and 850 to 1190 micrometers particle size ranges being used for further evaluation, designated as Components 5a, 5b, and 5c respectively.

f. Wood Pulp Fluff (Component 6)

Commercial kraft wood pulp fluff, consisting of about 16 weight percent southern hardwood and about 84 weight percent southern softwood, was obtained from Alliance Paper Company, Coosa Pines, Ala., under the designation CR 1654 wood pulp fluff, and used as a fibrous matrix containment material to make absorbent structures for further evaluation. The wood pulp fluff had a Free Swell value of about 6 grams per gram and an Absorbency Under Load value of about 4 grams per gram.

g. Wood Pulp Fluff (Component 7)

Commercial wood pulp fluff, consisting of about 10 weight percent hardwood and about 90 weight percent southern softwood, was obtained from Weyerhaeuser Company, Miss., under the designation NB 416 wood pulp fluff, and used as a fibrous matrix containment material to make absorbent structures for further evaluation. The wood pulp fluff had a Free Swell value of about 6 grams per gram and an Absorbency Under Load value of about 4 grams per gram.

h. PolyDiallyl Dimethyl Ammonium Hydroxide (Component 8)

About 2.1 grams of methylenebisacrylamide was dissolved as the crosslinking agent in 370 milliliters of 60 percent by weight aqueous solution of diallyidimethylammonium chloride monomer in a 1000 milliliters conical flask. The solution was purged with nitrogen for 15 minutes and the conical flask was stoppered and placed in a water bath at 60° C. Polymerization was initiated by the addition of 0.4 gram of potassium persulfate and 1.5 grams of sodium bisulfite to the reaction mixture. Polymerization was continued for 12 hours at 60° C. followed by cutting the gel that was formed into small pieces (about one inch cubes). The gel pieces were washed with 2 percent by weight sodium hydroxide solution until all the chloride ions in the polymer were exchanged for hydroxide ions. The completion of exchange was confirmed by testing the effluent after treatment with acidified silver nitrate to detect for chloride ions. The absence of chloride ions was taken as an indication of completion of conversion to the desired hydroxide form. The gel was washed thoroughly with distilled water until the pH of the distilled water after washing was the same as the water used for washing. The gel was dried at 50° C. overnight and ground using a blender from Warring (Model 34BL97). The ground polymer was sieved and the four different particle size ranges (300 to 600 micrometers, 600 to 850 micrometers, and 850 to 1190 micrometers) were used for further evaluation, designated as Components 8a, 8b, and 8c respectively. The polydiallyl dimethyl ammonium hydroxide polymer had a Free Swell value of about 26 grams per gram and an Absorbency Under Load value of about 18 grams per gram.

i. Chitosan (Component 9)

Forty grams of chitosan flake, available from Vanson Company under the designation VSN-608 chitosan, were mixed with 2000 grams of 1 weight percent acetic acid solution in a mixer manufactured by KitchenAid (Model K45SS). About 0.3 gram of poly(ethylene glycol) diglycidyl ether having a molecular weight of about 400 was added into the chitosan acetate solution as a crosslinking agent. The solution was then dried at 60° C. for at least 30 hours and ground into particulate and then sieved, with the 300 to 600 micrometers particle size range being used for further evaluation. The chitosan acetate particles were suspended in a 1 weight percent sodium hydroxide solution with a ratio of a gram of chitosan acetate to 100 grams of the sodium hydroxide solution. Under continuous stirring, using a magnetic stirrer, the chitosan acetate was converted into chitosan within at least 5 hours. The treated chitosan particles were then washed with distilled water four times with a ratio of chitosan to water 1 to 1000 to completely remove residual sodium acetate and sodium hydroxide. The washed chitosan was dried at 80° C. The chitosan polymer had a Free Swell value of about 3 grams per gram and an Absorbency Under Load value of about 2 grams per gram.

Example 1

Absorbent structures were prepared using an air-laying process. The absorbent structures had a basis weight of about 500 grams per square meter, a density of about 0.2±0.01 gram per cubic centimeter, and generally comprised about 37 weight percent of particulate material (Components 1–5, 8–9) and about 63 weight percent of wood pulp fluff (Components 6, 7). The composition of each absorbent structure sample is summarized in Table 1 and Table 2.

The absorbent structures were densified by a laboratory press, available from Fred S. Carver, Inc. in Wabash, Ind., under the designation Model 2333 laboratory press, at room temperature under about 10,000 to 15,000 psi for about 10 seconds. The absorbent structures were cut into 2 inches by 13.75 inches samples using a textile saw, available from Eastman Machine Company in Buffalo, N.Y., under the designation Chickadee II Rotary Shear, Type D-2, 110 volt textile saw.

The density of each absorbent structure sample was measured by its thickness before the absorbency and pH evaluations. If the density is too low, the absorbent structure sample was re-densified to the acceptable range. The absorbent structure sample was then placed into the testing apparatus for measurement of pH profile and Wicking Capacity values. In this example, the pH profile and the Wicking Capacity values were measured using a time period of 2.5 hours, instead of the 6 hour time period as specified in the Test Methods section. The results of the evaluations are shown in Table 3. Several of the absorbent structure samples were also evaluated for absorbency and pH properties over a time period of about 24 hours. For absorbent structure samples that did not comprise a buffering agent, or an effective amount of a buffering agent, wider variations in the pH values were generally observed over the 24 hour time period as compared to the 2.5 hour time period. For absorbent structure samples of the present invention that did comprise an effective amount of a buffering agent, no substantial difference in the liquid absorbency or pH values was observed between the two time periods.

TABLE 1

| Absorbent Structure Sample No. | Component 1 | Component 2b | Component 3 | Component 4 | Component 5a | Component 6 |
|---|---|---|---|---|---|---|
| *Sample 1 | 18.5 g | — | — | — | — | 31.2 g |
| *Sample 2 | — | 18.5 g | — | — | — | 31.2 g |
| *Sample 3 | — | — | 18.5 g | — | — | 31.2 g |
| *Sample 4 | — | 9.6 g | 8.9 g | — | — | 31.2 g |
| Sample 5 | — | 9.6 g | 8.9 g | — | 1.0 g | 31.2 g |
| *Sample 6 | — | 10.2 g | 8.3 g | — | — | 31.2 g |
| *Sample 7 | — | 10.2 g | 8.3 g | — | 0.5 g | 31.2 g |
| Sample 8 | — | 10.2 g | 8.3 g | — | 1.8 g | 31.2 g |
| Sample 9 | — | 10.2 g | 8.3 g | — | 3.5 g | 31.2 g |
| Sample 10 | — | 10.2 g | 8.3 g | — | 5.0 g | 31.2 g |
| *Sample 11 | — | 10.2 g | 8.3 g | — | 10.0 g | 31.2 g |
| *Sample 12 | — | 10.7 g | — | 7.8 g | — | 31.2 g |
| *Sample 13 | — | 10.7 g | — | 7.8 g | 1.8 g | 31.2 g |
| Sample 14 | — | 10.7 g | — | 7.8 g | 10.0 g | 31.2 g |

*Not an example of the present invention.

TABLE 2

| Absorbent Structure Sample No. | Comp. 1 | Comp. 8 | Comp. 9 | Comp. 2b | Comp. 5a | Comp. 3 | Comp. 6 | Comp. 7 |
|---|---|---|---|---|---|---|---|---|
| *Sample 15 | — | 18.5 g | — | — | — | — | — | 31.2 g |
| *Sample 16 | — | — | 18.5 g | — | — | — | 31.2 g | — |
| *Sample 17 | — | — | — | 18.5 g | — | — | 31.2 g | — |
| *Sample 18 | — | 12.3 g | — | 6.3 g | — | — | — | 31.2 g |
| Sample 19 | — | 12.3 g | — | 6.3 g | 0.5 g | — | — | 31.2 g |
| Sample 20 | — | 12.3 g | — | 6.3 g | 2.0 g | — | — | 31.2 g |
| *Sample 21 | — | 12.3 g | — | 6.3 g | 3.0 g | — | — | 31.2 g |
| *Sample 22 | — | — | 11.2 g | 7.3 g | — | — | 31.2 g | — |
| Sample 23 | — | — | 11.2 g | 7.3 g | — | 0.5 g | 31.2 g | — |
| *Sample 24 | — | — | 11.2 g | 7.3 g | — | 2.0 g | 31.2 g | — |

*Not an example of the present invention.

TABLE 3

| Absorbent Structure Sample No. | Wicking Capacity value (g/g) | pH Range at 0.6 cm | pH Range at 5 cm | pH Range at 10 cm | pH Range at 15 cm | pH Range at 20 cm | pH Range at 25 cm |
|---|---|---|---|---|---|---|---|
| *Sample 1 | 12.5 | 5.8–5.9 | 5.9–6.0 | 5.6–5.8 | 5.1–5.8 | 4.3–5.6 | 4.7–5.5 |
| *Sample 2 | 6.8 | 2.2–2.5 | 2.5–2.8 | 2.7–2.8 | 2.3–2.4 | 2.0–2.1 | — |
| *Sample 3 | 4.8 | 7.6–7.8 | 8.2–8.3 | 7.7–8.6 | 7.1–8.5 | 6.8–8.3 | 7.7–8.9 |
| *Sample 4 | 10.5 | 5.5–6.5 | 4.9–6.5 | 5.2–6.9 | 5.8–6.9 | 7.2–8.4 | 7.2–8.7 |
| Sample 5 | 9.9 | 4.2–5.0 | 4.7–6.3 | 4.9–6.1 | 5.9–6.7 | 6.3–6.8 | 6.4–7.3 |
| *Sample 6 | 11.9 | 5.3–6.0 | 4.3–5.5 | 5.1–6.3 | 6.0–6.2 | 5.9–7.1 | 6.7–8.1 |
| *Sample 7 | 12.1 | 4.7–5.2 | 4.8–6.0 | 6.1–6.4 | 4.7–6.8 | 5.5–7.8 | 6.5–8.4 |
| Sample 8 | 10.9 | 5.3–6.4 | 5.5–6.5 | 5.9–6.6 | 4.3–6.4 | 6.3–6.8 | 5.2–6.0 |
| Sample 9 | 11.2 | 4.6–5.0 | 4.4–5.6 | 5.4–6.3 | 3.3–5.6 | 4.2–5.6 | 4.0–5.7 |
| Sample 10 | 9.8 | 4.6–5.3 | 4.4–6.1 | 4.9–5.9 | 5.2–5.3 | 4.6–4.9 | 4.4–4.7 |
| *Sample 11 | 8.7 | 3.4–3.5 | 4.3–4.5 | 3.5–3.8 | 1.6–4.0 | 3.3–4.7 | 2.6–4.1 |
| *Sample 12 | 11.0 | 5.0–8.0 | 4.5–6.4 | 5.2–7.2 | 6.4–7.5 | 6.9–7.5 | 8.1–8.8 |
| *Sample 13 | 9.2 | 4.3–5.8 | 4.3–6.3 | 4.8–6.3 | 5.8–6.5 | 7.1–7.6 | 7.4–8.3 |
| Sample 14 | 9.9 | 4.2–4.6 | 4.5–5.2 | 4.5–4.9 | 4.7–4.8 | 5.0–5.6 | 4.8–5.2 |
| *Sample 15 | 12.6 | 9.3–9.7 | 9.5–9.7 | 9.4–9.6 | 9.0–9.7 | — | — |
| *Sample 16 | 5.8 | 7.1–8.6 | 6.8–8.7 | 7.3–8.4 | 7.4–8.1 | 7.9–8.4 | — |
| *Sample 17 | 6.8 | 2.2–2.5 | 2.5–2.8 | 2.7–2.8 | 2.3–2.4 | 2.0–2.1 | — |
| *Sample 18 | 10.5 | 5.6–8.6 | 5.0–7.3 | 4.3–5.9 | 6.7–8.6 | 6.1–6.2 | — |
| Sample 19 | 9.9 | 4.6–5.6 | 4.7–6.1 | 5.4–6.7 | 5.1–5.9 | 4.9–5.4 | — |
| Sample 20 | 7.7 | 4.3–5.1 | 4.1–5.1 | 3.4–3.7 | 3.4–3.5 | — | — |
| *Sample 21 | 6.8 | 3.7–4.6 | 3.8–4.2 | 3.0–3.3 | 2.9–3.5 | 3.2–3.3 | — |
| *Sample 22 | 9.6 | 4.3–5.8 | 4.1–5.6 | 4.2–5.4 | 2.7–5.3 | 4.2–4.7 | — |
| Sample 23 | 9.7 | 5.4–5.7 | 4.6–5.3 | 5.1–6.1 | 5.6–7.2 | 5.7–5.8 | — |
| *Sample 24 | 8.6 | 5.9–6.5 | 5.6–6.1 | 6.2–6.7 | 7.1–9.2 | 7.6–9.5 | — |

*Not an example of the present invention.

Example 2

Absorbent structures were prepared using an air-laying process. The absorbent structures had a basis weight of about 500 grams per square meter, a density of about 0.2±0.01 gram per cubic centimeter, and generally comprised about 37 weight percent of particulate material (Components 2, 3, 5, and 8) and about 63 weight percent of wood pulp fluff (Component 6). The composition of each absorbent structure sample is summarized in Table 4.

The absorbent structures were densified by a laboratory press, available from Fred S. Carver, Inc. in Wabash, Ind., under the designation Model 2333 laboratory press, at room temperature under about 10,000 to 15,000 psi for about 10 seconds. The absorbent structures were cut into 2 inches by 13.75 inches samples using a textile saw, available from Eastman Machine Company in Buffalo, N.Y., under the designation Chickadee II Rotary Shear, Type D-2, 110 volt textile saw.

The density of each absorbent structure sample was measured by its thickness before the absorbency and pH evaluations. If the density is too low, the absorbent structure sample was re-densified to the acceptable range. The absorbent structure sample was then placed into the testing apparatus for measurement of pH profile and Wicking Capacity values. The results of the evaluations are shown in Table 5. In Table 5, $I_a$ represents the Ionization Rate for the acidic polymer or acidic second material used in the absorbent structure sample. $I_b$ represents the Ionization Rate for the basic polymer or basic second material used in the absorbent structure sample.

Example 3

Absorbent structures were prepared using an air-laying process. The absorbent structures had two layers and a total basis weight of about 500 grams per square meter, a density of about 0.2±0.01 gram per cubic centimeter, and generally comprised about 37 weight percent of particulate material (Components 2, 3, 5, and 8) and about 63 weight percent of wood pulp fluff (Component 6). The two layered absorbent structure was made by first forming a lower layer of particulate material and wood pulp fluff, and then forming an upper layer of particulate material and wood pulp fluff on the top of the lower layer. The composition of each absorbent structure sample is summarized in Table 6.

The layered absorbent structures were densified by a laboratory press, available from Fred S. Carver, Inc. in Wabash, Ind., under the designation Model 2333 laboratory press, at room temperature under about 10,000 to 15,000 psi for about 10 seconds. The absorbent structures were cut into 2 inches by 13.75 inches samples using a textile saw, available from Eastman Machine Company in Buffalo, N.Y., under the designation Chickadee II Rotary Shear, Type D-2, 110 volt textile saw.

The density of each absorbent structure sample was measured by its thickness before the absorbency and pH evaluations. If the density is too low, the absorbent structure sample was re-densified to the acceptable range. The absorbent structure sample was then placed into the testing apparatus for measurement of pH profile and Wicking Capacity values. The surface of the upper layer is in contact with the pH probes. The results of the evaluations are shown in Table 7.

TABLE 4

| Absorbent Structure Sample No. | Component 2a | Component 2b | Component 2c | Component 2d | Component 3 | Component 6 |
|---|---|---|---|---|---|---|
| Sample 25 | 10.2 g | — | — | — | 8.5 g | 31.2 g |
| *Sample 26 | — | 10.2 g | — | — | 8.5 g | 31.2 g |
| *Sample 27 | — | — | 10.2 g | — | 8.5 g | 31.2 g |
| *Sample 28 | — | — | — | 10.2 g | 8.5 g | 31.2 g |

| | Component 8a | Component 8b | Component 8c | | Component 5c | Component 6 |
|---|---|---|---|---|---|---|
| *Sample 29 | 9.5 g | — | — | — | 9.0 g | 31.2 g |
| Sample 30 | — | 9.5 g | — | — | 9.0 g | 31.2 g |
| *Sample 31 | — | — | 9.5 g | — | 9.0 g | 31.2 g |

*Not an example of the present invention.

TABLE 5

| Absorbent Structure Sample No. | $I_a$ (min$^{-1}$) | $I_b$ (min$^{-1}$) | Wicking Capacity value (g/g) | pH Range at 0.6 cm | pH Range at 5 cm | pH Range at 10 cm | pH Range at 15 cm | pH Range at 20 cm | pH Range at 25 cm |
|---|---|---|---|---|---|---|---|---|---|
| Sample 25 | 9.01 | 8.94 | 12.0 | 5.6–6.3 | 5.4–6.4 | 6.2–6.9 | 6.9–7.0 | 7.1–7.5 | 5.9–7.7 |
| *Sample 26 | 8.72 | 8.94 | 11.2 | 5.4–6.6 | 5.6–6.7 | 5.9–6.8 | 6.4–6.8 | 6.6–7.6 | 6.3–8.5 |
| *Sample 27 | 6.75 | 8.94 | 9.4 | 5.8–6.5 | 5.1–6.8 | 5.8–6.7 | 6.4–7.5 | 7.2–7.9 | 6.6–8.9 |
| *Sample 28 | 6.64 | 8.94 | 9.7 | 4.7–7.1 | 5.1–6.7 | 4.8–7.1 | 6.8–7.5 | 7.8–8.8 | 7.7–8.3 |
| *Sample 29 | 9.74 | 12.00 | 7.7 | 4.5–8.7 | 4.2–5.2 | 3.7–5.4 | 3.7–4.9 | 3.1–3.4 | 3.6–4.9 |
| Sample 30 | 9.74 | 9.78 | 7.3 | 3.8–4.7 | 4.1–5.1 | 3.6–4.7 | 3.2–4.1 | 3.3–4.0 | — |
| *Sample 31 | 9.74 | 8.51 | 8.1 | 4.6–5.4 | 2.5–4.3 | 3.2–5.0 | 2.8–4.4 | 3.2–3.5 | 4.3–6.6 |

*Not an example of the present invention.

While the present invention has been described in terms of the specific embodiments described above, numerous equivalent changes and modifications will be clear to those skilled in the art. Accordingly, the specific examples set forth above are not intended to limit in any manner the scope of the invention as set forth in the appended claims.

TABLE 6

| Absorbent Structure Sample No. | Component 2b Upper Layer | Component 2b Lower Layer | Component 3 Upper Layer | Component 3 Lower Layer | Component 8c Upper Layer | Component 8c Lower Layer | Component 5c Upper Layer | Component 5c Lower Layer | Component 6 Upper Layer | Component 6 Lower Layer |
|---|---|---|---|---|---|---|---|---|---|---|
| *Sample 32 | 10.2 | — | — | 8.5 | — | — | — | — | 15.6 | 15.6 |
| *Sample 33 | — | 10.2 | 8.5 | — | — | — | — | — | 15.6 | 15.6 |
| Sample 34 | 10.2 | — | — | 8.5 | — | — | — | — | 20.8 | 10.4 |
| *Sample 35 | — | 10.2 | 8.5 | — | — | — | — | — | 10.4 | 20.8 |
| *Sample 36 | — | — | — | — | 9.5 | — | — | 9.0 | 15.6 | 15.6 |
| *Sample 37 | — | — | — | — | — | 9.5 | 9.0 | — | 15.6 | 15.6 |
| Sample 38 | — | — | — | — | 9.5 | — | — | 9.0 | 20.8 | 10.4 |
| *Sample 39 | — | — | — | — | — | 9.5 | 9.0 | — | 10.4 | 20.8 |

*Not an example of the present invention.

TABLE 7

| Absorbent Structure Sample No. | Wicking Capacity value (g/g) | pH Range at 0.6 cm | pH Range at 5 cm | pH Range at 10 cm | pH Range at 15 cm | pH Range at 20 cm | pH Range at 25 cm |
|---|---|---|---|---|---|---|---|
| *Sample 32 | 9.0 | 3.6–4.4 | 3.9–6.6 | 4.1–7.3 | 6.1–7.3 | 7.0–8.4 | 5.3–7.9 |
| *Sample 33 | 9.4 | 6.0–7.5 | 4.2–7.0 | 5.6–7.8 | 6.2–7.2 | 7.0–8.2 | 7.1–8.4 |
| Sample 34 | 10.0 | 3.4–4.4 | 3.9–5.3 | 4.3–6.1 | 6.2–7.0 | 7.0–7.7 | 6.5–7.8 |
| *Sample 35 | 8.1 | 5.8–7.5 | 5.7–7.0 | 5.5–6.9 | 6.1–7.3 | 4.8–7.4 | 5.7–8.1 |
| *Sample 36 | 7.8 | 5.0–6.3 | 3.9–5.5 | 4.0–6.3 | 2.9–4.3 | 2.9–3.6 | 3.8–4.7 |
| *Sample 37 | 7.7 | 2.1–3.3 | 2.2–3.7 | 2.3–3.9 | 2.4–3.7 | 3.0–3.2 | 3.0–3.3 |
| Sample 38 | 9.3 | 4.3–5.8 | 3.5–5.4 | 3.4–5.9 | 3.4–4.8 | 3.8–4.6 | 3.6–3.8 |
| *Sample 39 | 7.9 | 2.2–4.8 | 2.8–6.3 | 2.7–6.4 | 2.7–4.7 | 3.0–3.7 | — |

*Not an example of the present invention.

What is claimed is:

1. An absorbent structure having an upper surface, the absorbent structure comprising:
   a) a water-swellable, water-insoluble polymer having acidic functional groups, wherein the water-swellable, water-insoluble polymer has at least about 50 molar percent of the acidic functional groups in free acid form; and
   b) a non-polymeric basic material;
wherein the absorbent structure exhibits a Wicking Capacity value that is at least about 5 grams per gram of absorbent structure and exhibits a pH on the upper surface that remains within the range of about 3 to about 8.

2. The absorbent structure of claim 1 wherein the non-polymeric basic material comprises an organic salt, an aliphatic amine, an aromatic amine, an aliphatic imine, an aromatic imine, an aliphatic amide, an aromatic amide, a metallic oxide, a hydroxide, an inorganic salt, or mixtures thereof.

3. The absorbent structure of claim 1 wherein the basic material is sodium citrate.

4. The absorbent structure of claim 1 wherein the basic material is sodium carbonate, sodium bicarbonate, or calcium carbonate.

5. The absorbent structure of claim 1 wherein the acidic water-swellable, water-insoluble polymer has a pKa between about 2 and about 10.

6. The absorbent structure of claim 1 wherein the acidic water-swellable, water-insoluble polymer has at least about 70 molar percent of the acidic functional groups in free acid form.

7. The absorbent structure of claim 1 wherein the acidic water-swellable, water-insoluble polymer is prepared from a base comprising polyacrylamide, polyvinyl alcohol, ethylene maleic anhydride copolymer, polyvinylether, polyacrylic acid, polyvinylpyrrolidone, polyvinylmorpholine, carboxymethyl cellulose, carboxymethyl starch, hydroxypropyl cellulose, algin, alginate, carrageenan, acrylic grafted starch, acrylic grafted cellulose, polyaspartic acid, polyglutamic acid, and copolymers thereof.

8. The absorbent structure of claim 1 wherein the acidic water-swellable, water-insoluble polymer comprises carboxyl groups, sulfonic groups, sulphate groups, sulfite groups, phosphate groups, or combinations thereof.

9. The absorbent structure of claim 7 wherein the acidic water-swellable, water-insoluble polymer and the basic material are present in the absorbent structure in a molar ratio from about 10:1 to about 1:10.

10. The absorbent structure of claim 7 wherein the absorbent structure exhibits a Wicking Capacity value that is at least about 10 grams per gram of absorbent structure.

11. The absorbent structure of claim 7 wherein the absorbent structure exhibits a pH on the upper surface that remains within the range of about 4 to about 7.

12. The absorbent structure of claim 1 further comprising a liquid-permeable topsheet and a backsheet attached to the topsheet, wherein the absorbent structure is positioned between the liquid-permeable topsheet and the backsheet.

* * * * *